US012745977B2

(12) United States Patent
Horiuchi et al.

(10) Patent No.: US 12,745,977 B2
(45) Date of Patent: Sep. 29, 2026

(54) MEDICAL IMAGING APPARATUS, MEDICAL IMAGING METHOD, MEDICAL IMAGING PROGRAM, AND MEDICAL IMAGING SYSTEM

(71) Applicant: FUJIFILM Corporation, Tokyo (JP)

(72) Inventors: Hisatsugu Horiuchi, Kanagawa (JP); Atsushi Osawa, Kanagawa (JP); Rika Tashiro, Kanagawa (JP); Takeyasu Kobayashi, Kanagawa (JP); Sayaka Saito, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 44 days.

(21) Appl. No.: 18/931,564

(22) Filed: Oct. 30, 2024

(65) Prior Publication Data

US 2025/0143666 A1 May 8, 2025

(30) Foreign Application Priority Data

Nov. 7, 2023 (JP) ................................ 2023-190077

(51) Int. Cl.
*A61B 8/00* (2006.01)
*A61B 8/08* (2006.01)

(52) U.S. Cl.
CPC ............ *A61B 8/0825* (2013.01); *A61B 8/403* (2013.01); *A61B 8/4254* (2013.01); *A61B 8/4281* (2013.01); *A61B 8/4461* (2013.01); *A61B 8/463* (2013.01); *A61B 8/54* (2013.01)

(58) Field of Classification Search
CPC ..... A61B 8/0825; A61B 8/403; A61B 8/4254; A61B 8/4281; A61B 8/4461; A61B 8/463; A61B 8/54
See application file for complete search history.

(56) References Cited

U.S. PATENT DOCUMENTS

2005/0089205 A1 4/2005 Kapur et al.
2008/0249415 A1* 10/2008 Okamura ............ A61B 8/5207 600/445
2008/0255452 A1 10/2008 Entrekin
2014/0135623 A1* 5/2014 Manak ................ A61B 8/5261 600/427
2017/0281124 A1* 10/2017 Arai ..................... A61B 8/0825
2023/0042741 A1 2/2023 Rohling et al.

FOREIGN PATENT DOCUMENTS

JP 2005-125080 A 5/2005
JP 2008-514264 A 5/2008
JP 2023-510931 A 3/2023

* cited by examiner

*Primary Examiner* — Amal Aly Farag
(74) *Attorney, Agent, or Firm* — Studebaker Brackett PLLC

(57) ABSTRACT

A medical imaging apparatus includes a processor that acquires a position of an ultrasound probe that emits an ultrasound beam toward a breast of an examinee, which is in a compressed state by way of a compression plate. The processor detects a distance in a direction orthogonal to a side surface of the compression plate on a chest wall side to the ultrasound probe based on the position of the ultrasound probe. When the distance is equal to or smaller than a predetermined distance from the side surface, the processor controls switching to a steer mode or a trapezoidal mode in which an emission direction of the ultrasound beam is directed toward the chest wall side.

14 Claims, 16 Drawing Sheets

MEDICAL IMAGING APPARATUS, MEDICAL IMAGING METHOD, MEDICAL IMAGING PROGRAM, AND MEDICAL IMAGING SYSTEM

CROSS-REFERENCE TO RELATED APPLICATIONS

This application claims priority under 35 USC 119 from Japanese Patent Application No. 2023-190077 filed on Nov. 7, 2023, the disclosure of which is incorporated by reference herein

BACKGROUND

1. Technical Field

The present disclosure relates to a medical imaging apparatus, a medical imaging method, a medical imaging program, and a medical imaging system.

2. Description of the Related Art

JP2005-125080A discloses a method of observing an abnormal part (152) in different types of images, the method including: a step of scanning an object using a first imaging system (20) to obtain at least a first image (58) of the object; a step of determining coordinates of a region of interest (ROI) (160) that can be observed on the first image (158), the ROI (160) including the abnormal part (152); and a step of using the coordinates of the ROI (160) to scan the object using a second imaging system (14).

JP2008-514264A discloses a method of executing an ultrasound image diagnosis of a breast with high accuracy, the method including a step of preparing a first compression plate, and a step of preparing a second compression plate, in which the first compression plate and the second compression plate receive the breast, the breast is compressed between the first compression plate and the second compression plate, the breast extends from a chest wall on a proximal end side of a patient toward a nipple on a distal end side, a portion of the breast close to the nipple and a portion of the breast close to an outer edge of the breast are not in contact with the second compression plate while the breast is being compressed, the method includes a step of moving an ultrasound transducer array, which is disposed on a side opposite to the breast with respect to the second compression plate and is adjacent to the second compression plate, along a path to scan the breast, and a step of acquiring image data representing the breast by moving the ultrasound transducer array along the path, and the acquiring step includes a step of operating a direction of an electronic beam with the ultrasound transducer array to acquire image data of one or two of (i) a portion of the breast close to the chest wall or (ii) a portion of the breast, which is not in contact with the second compression plate.

JP2023-510931A discloses an apparatus comprising (i) a substrate that is at least 77.4% transparent to ionizing radiation, and (ii) an array of polymer-based capacitive nanofabrication ultrasound transducers disposed on the substrate, the array including a first row of the transducers and electrical interconnections electrically connecting the transducers of the first row in series.

SUMMARY

In the related art, a medical imaging system has been known, which has both a function of capturing a radiation image by emitting radiation from a radiation source toward a subject, such as a breast of an examinee, and detecting the radiation transmitted through the subject via a radiation detector, and a function of capturing an ultrasound image of the breast by scanning the breast with an ultrasound probe along the breast of the examinee using ultrasound.

In such a medical imaging system, in a case in which the scanning using the ultrasound probe is performed on the compression plate to capture the ultrasound image in a state in which the breast is compressed by the compression plate, there is a problem in that the ultrasound beam does not sufficiently reach a chest wall side, and it is difficult to acquire the ultrasound image on the chest wall side.

An object of the present disclosure is to provide a medical imaging apparatus, a medical imaging method, a medical imaging program, and a medical imaging system capable of facilitating acquisition of an ultrasound image on a chest wall side.

In order to achieve the above-described object, a first aspect of the present disclosure provides a medical imaging apparatus comprising: a processor, in which the processor is configured to: acquire a position of an ultrasound probe that emits an ultrasound beam toward a breast of an examinee, which is in a compressed state via a compression plate; and in a case in which the position of the ultrasound probe in a direction orthogonal to a side surface of the compression plate on a chest wall side is equal to or smaller than a predetermined distance from the side surface and a predetermined switching condition is satisfied, perform control of switching to a steer mode or a trapezoidal mode in which an emission direction of the ultrasound beam is directed toward the chest wall side.

A second aspect provides the medical imaging apparatus according to the first aspect, in which, in a case in which an inclination angle of the ultrasound beam emitted in the steer mode or the trapezoidal mode is denoted by $\theta$, a depth of the breast to be observed is denoted by a, and a distance between the ultrasound probe and the compression plate is denoted by b, the predetermined distance is a distance represented by $\tan\theta \times (a+b)$.

A third aspect provides the medical imaging apparatus according to the first or second aspect, in which the processor is configured to control a scanning mechanism that performs scanning using the ultrasound probe on the compression plate, and the switching condition is a case in which an instruction to stop capturing of an ultrasound image via the ultrasound probe is not received.

A fourth aspect provides the medical imaging apparatus according to the first or second aspect, in which the processor is configured to: set a specific region to be irradiated with the ultrasound beam based on a radiation image captured by emitting radiation to the breast of the examinee; and control a scanning mechanism that performs scanning using the ultrasound probe on the compression plate, and the switching condition is a case in which capturing of an ultrasound image via the ultrasound probe is not performed on the specific region.

A fifth aspect provides the medical imaging apparatus according to the first or second aspect, in which the switching condition is a case in which an instruction to stop capturing of an ultrasound image via the ultrasound probe is not received.

A sixth aspect provides the medical imaging apparatus according to any one of the first to fifth aspects, in which the compression plate includes a guide member that guides the ultrasound probe such that a longitudinal direction of the ultrasound probe is a direction orthogonal to a chest wall.

A seventh aspect provides the medical imaging apparatus according to any one of the first to fifth aspects, in which the processor is configured to control a scanning mechanism that performs scanning using the ultrasound probe on the compression plate such that the scanning using the ultrasound probe is performed on the compression plate in a state in which a longitudinal direction of the ultrasound probe is in the direction orthogonal to the side surface of the ultrasound probe on the chest wall side.

An eighth aspect provides the medical imaging apparatus according to any one of the first to seventh aspects, in which an acoustic matching material is provided between the ultrasound probe and the compression plate.

A ninth aspect provides the medical imaging apparatus according to the eighth aspect, in which a thickness of the acoustic matching material is 1 mm or larger and 10 mm or smaller.

A tenth aspect provides the medical imaging apparatus according to the eighth or ninth aspect, in which a thickness of the acoustic matching material is larger as a distance to the chest wall is smaller.

An eleventh aspect provides the medical imaging apparatus according to any one of the first to tenth aspects, in which the processor is configured to display, in a distinguishable manner on a display unit, a first imaging region imaged in a state in which the emission direction of the ultrasound beam is a normal direction and a second imaging region imaged in the steer mode or the trapezoidal mode in which the emission direction of the ultrasound beam is inclined, and display, on the display unit, a captured ultrasound image.

A twelfth aspect provides a medical imaging method comprising: via a computer, acquiring a position of an ultrasound probe that emits an ultrasound beam toward a breast of an examinee, which is in a compressed state via a compression plate; and performing, in a case in which the position of the ultrasound probe in a direction orthogonal to a side surface of the compression plate on a chest wall side is equal to or smaller than a predetermined distance from the side surface and a predetermined switching condition is satisfied, control of switching to a steer mode or a trapezoidal mode in which an emission direction of the ultrasound beam is directed toward the chest wall side.

A thirteenth aspect provides a medical imaging program causing a computer to execute a process comprising: acquiring a position of an ultrasound probe that emits an ultrasound beam toward a breast of an examinee, which is in a compressed state via a compression plate; and performing, in a case in which the position of the ultrasound probe in a direction orthogonal to a side surface of the compression plate on a chest wall side is equal to or smaller than a predetermined distance from the side surface and a predetermined switching condition is satisfied, control of switching to a steer mode or a trapezoidal mode in which an emission direction of the ultrasound beam is directed toward the chest wall side.

A fourteenth aspect provides a medical imaging system comprising: a mammography apparatus that captures a radiation image by detecting radiation, which is emitted from a radiation source and is transmitted through a breast of an examinee, via a radiation detector; an ultrasound probe that emits an ultrasound beam to the breast of the examinee; and the medical imaging apparatus according to any one of the first to eleventh aspects.

According to the present disclosure, it is possible to facilitate the acquisition of the ultrasound image on the chest wall side.

BRIEF DESCRIPTION OF THE DRAWINGS

Exemplary embodiments of the technology of the disclosure will be described in detail based on the following figures, wherein.

DETAILED DESCRIPTION

Hereinafter, embodiments of the present invention will be described in detail with reference to the accompanying drawings. It should be noted that each embodiment does not limit the invention.

First Embodiment

Figure 1:
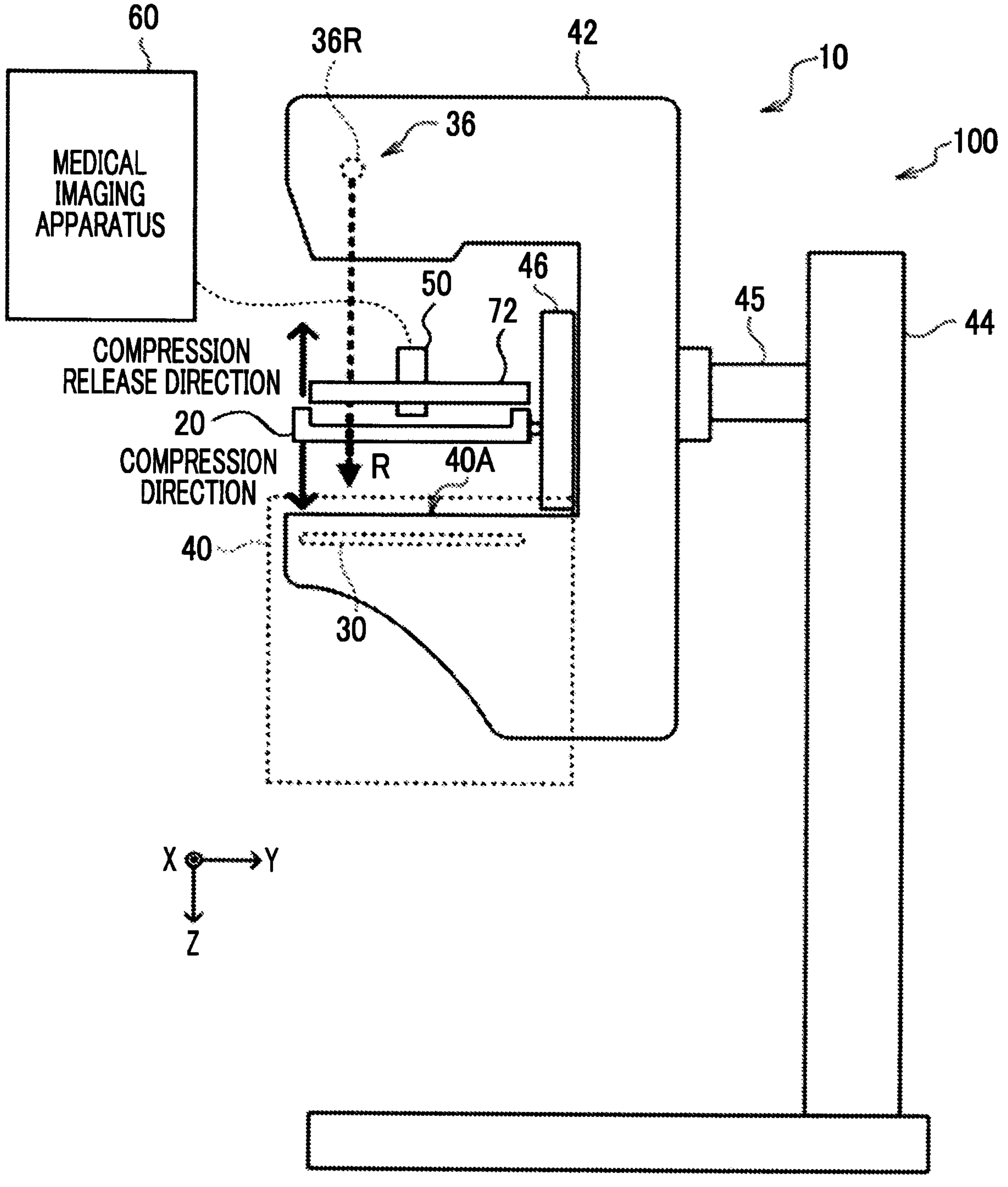
FIG. 1 is a diagram showing an example of a medical imaging system according to a first embodiment.

FIG. 1 is a diagram showing an example of a medical imaging system 100 according to the first embodiment. The medical imaging system 100 according to the present embodiment comprises a mammography apparatus 10, an ultrasound probe 50, and a medical imaging apparatus 60. It should be noted that, in FIG. 1, a depth direction is defined as an X axis direction, a left-right direction is defined as a Y axis direction, and an up-down direction is defined as a Z axis direction.

The mammography apparatus 10 according to the present embodiment is an apparatus that targets a breast of an examinee as a subject and captures a radiation image of the breast by irradiating the breast with radiation R (for example, X-rays). It should be noted that the mammography apparatus 10 may be an apparatus that images the breast of the examinee in a state (sitting state) in which the examinee is sitting on a chair (including a wheelchair) or the like in addition to a state (standing state) in which the examinee is standing.

As shown in FIG. 1, a mammography apparatus 10 according to the present embodiment comprises a compression plate 20, a radiation detector 30, a radiation emission unit 36, an imaging table 40, an arm part 42, a base 44, a shaft part 45, and a compression unit 46.

The radiation detector 30 detects the radiation R that has been transmitted through the breast of the examinee. The radiation detector 30 is disposed in the imaging table 40. In a case in which imaging is performed in the mammography apparatus 10 according to the present embodiment, the breast of the examinee is positioned on an imaging surface 40A of the imaging table 40 by a user such as a doctor or a radiologic technologist. For example, the imaging surface 40A or the like that is in contact with the breast of the examinee are made of carbon or the like in terms of the transmittance or the intensity of the radiation R.

The radiation detector 30 detects the radiation R transmitted through the breast of the examinee and the imaging table 40, generates the radiation image based on the detected radiation R, and outputs image data representing the generated radiation image. A type of the radiation detector 30 is not particularly limited and may be, for example, an indirect conversion type radiation detector that converts the radiation R into light and converts the converted light into a charge, or a direct conversion type radiation detector that directly converts the radiation R into a charge.

The radiation emission unit 36 comprises a radiation source 36R. The radiation emission unit 36 is provided on the arm part 42 together with the imaging table 40 and the compression unit 46. It should be noted that the mammography apparatus 10 comprises the arm part 42, the base 44, and the shaft part 45. The arm part 42 is held by the base 44 to be movable in the up-down direction (Z axis direction). The arm part 42 is connected to the base 44 by the shaft part 45. The compression unit 46 and the arm part 42 can be rotated relative to the base 44, separately, using the shaft part 45 as a rotation axis. In the present embodiment, gears (not shown) are provided in each of the shaft part 45, the arm part 42, and the compression unit 46, and the gears are switched between an engaged state and a disengaged state to connect each of the arm part 42 and the compression unit 46 to the shaft part 45. One or two of the arm part 42 or the compression unit 46 connected to the shaft part 45 are rotated integrally with the shaft part 45.

The compression plate 20 according to the present embodiment is moved in the up-down direction (Z axis direction) by a compression plate driving unit 32 to compress the breast of the examinee between the compression plate 20 and the imaging table 40. As shown in FIG. 1, in the movement direction of the compression plate 20, a direction of compressing the breast, in other words, a direction of approaching the imaging surface 40A is referred to as a "compression direction". In addition, a direction of releasing the compression of the breast, in other words, a direction of approaching the radiation emission unit 36 is referred to as a "compression release direction".

It is preferable that the compression plate 20 is optically transparent in order to check positioning or a compressed state in the compression of the breast, and the compression plate 20 is made of a material having high transmittance for the radiation R. Further, it is desirable that the compression plate 20 is made of a material that facilitates the transmission of the ultrasound from the ultrasound probe 50. Examples of the material forming the compression plate 20 include resins such as polymethylpentene, polycarbonate, acrylic, and polyethylene terephthalate. In particular, polymethylpentene is suitable as the material forming the compression plate 20 since polymethylpentene has low rigidity, high elasticity, and high flexibility and has suitable values for acoustic impedance that affects the reflectance of the ultrasound and an attenuation coefficient that affects the attenuation of the ultrasound.

It should be noted that the compression plate 20 is not limited to the compression plate that compresses the entire breast, but may be the compression plate that compresses a part of the breast. In other words, the compression plate 20 may be smaller than the breast. As such a compression plate 20, for example, a compression plate 20 used for so-called spot imaging is known in which a radiation image of only a region in which a lesion exists is captured.

On the other hand, the medical imaging apparatus 60 is an apparatus that is connected to the ultrasound probe 50 and targets the breast of the examinee as the subject to capture an ultrasound image.

The ultrasound probe 50 is moved on the compression plate 20 by a scanning mechanism 72 provided above the compression plate 20, and acquires the ultrasound image of the breast by scanning the breast with ultrasound.

The ultrasound probe 50 comprises a plurality of ultrasound transducers arranged one-dimensionally or two-dimensionally. Each of the ultrasound transducers transmits the ultrasound based on an applied driving signal, receives an ultrasound echo, and outputs a reception signal.

Each of the plurality of ultrasound transducers includes, for example, a transducer in which electrodes are formed at both ends of a piezoelectric material (piezoelectric body) such as a piezoelectric ceramic represented by lead (Pb) zirconate titanate (PZT) or a polymer piezoelectric element represented by polyvinylidene difluoride (PVDF). In a case in which the pulsed or continuous wave driving signal is transmitted to apply a voltage to the electrodes of the transducer, the piezoelectric body is expanded and contracted. The pulsed or continuous wave ultrasound is generated from each transducer by the expansion and contraction and these types of the ultrasound are synthesized to form an ultrasound beam. Each transducer receives the propagating ultrasound and is then expanded and contracted to generate an electric signal. The electric signal is output as an ultrasound reception signal and then input to the medical imaging apparatus 60 through a cable indicated by a dotted line.

Figure 2:
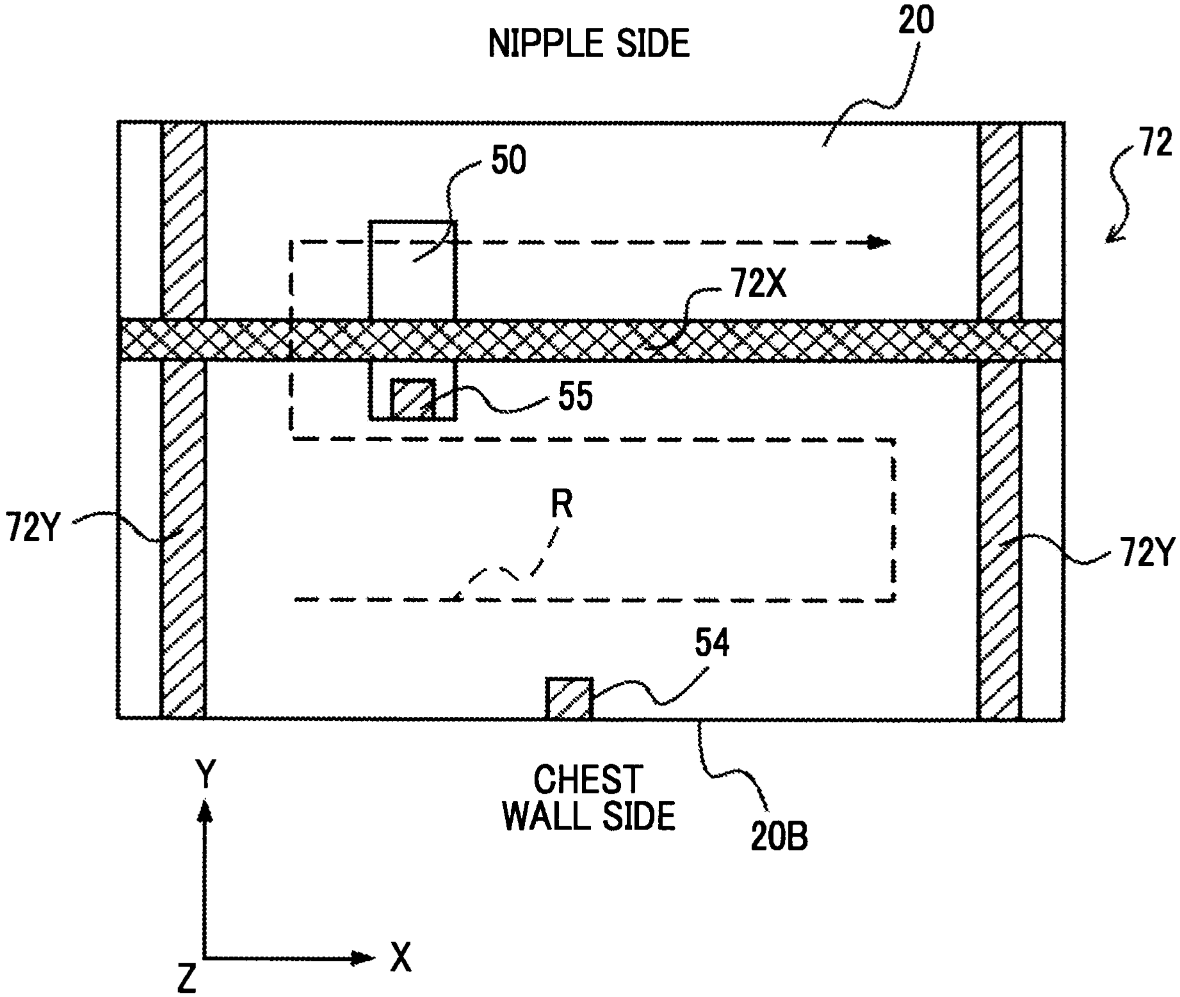
FIG. 2 is a top view showing an example of a scanning mechanism according to the first embodiment.

As shown in FIG. 2, the scanning mechanism 72 has a function of moving the ultrasound probe 50 in a front-rear direction along a Y axis, a left-right direction along a X axis, and an up-down direction along a Z axis. The scanning mechanism 72 includes one movement rail 72X and two movement rails 72Y. The movement rail 72X is a rail that extends along the X axis, and the ultrasound probe 50 is attached to the movement rail 72X. A position of the ultrasound probe 50 can be changed along the X axis by moving the ultrasound probe 50 along the movement rail 72X. That is, the scanning using the ultrasound probe 50 can be performed along the X axis.

In addition, the movement rails 72Y are rails that are provided on both end sides of the compression plate 20 and extend along the Y axis. The scanning mechanism 72 can change the position of the ultrasound probe 50 along the Y axis by moving the movement rails 72X to which the ultrasound probe 50 is attached, along the Y axis. That is, the scanning using the ultrasound probe 50 can be performed along the Y axis.

In addition, the scanning mechanism 72 can also change a height of the ultrasound probe 50 by moving the movement rails 72X and 72Y along the Z axis.

In addition, in the example of FIG. 2, the ultrasound probe 50 is attached to the movement rail 72X such that a longitudinal direction of the ultrasound probe 50 is a direction orthogonal to a side surface 20B of the compression plate 20 on the chest wall side. In this case, for example, as shown in FIG. 2, the scanning using the ultrasound probe 50 is performed by the scanning mechanism 72 to move along a predetermined route R. The route R is a route in which a distance in which the ultrasound probe 50 moves along a direction orthogonal to the longitudinal direction of the ultrasound probe 50 is larger than a distance in which the ultrasound probe 50 moves along a lateral direction of the ultrasound probe 50. Therefore, the entire region can be scanned in short time.

It should be noted that the ultrasound probe 50 may be attached to the movement rail 72X such that the lateral direction of the ultrasound probe 50 is a direction orthogonal to the side surface 20B of the compression plate 20 on the chest wall side. In this case, a high-resolution ultrasound image is obtained as compared with a case in which the ultrasound probe 50 is attached to the movement rail 72X such that the longitudinal direction of the ultrasound probe 50 is a direction orthogonal to the side surface 20B of the compression plate 20 on the chest wall side.

Figure 3:
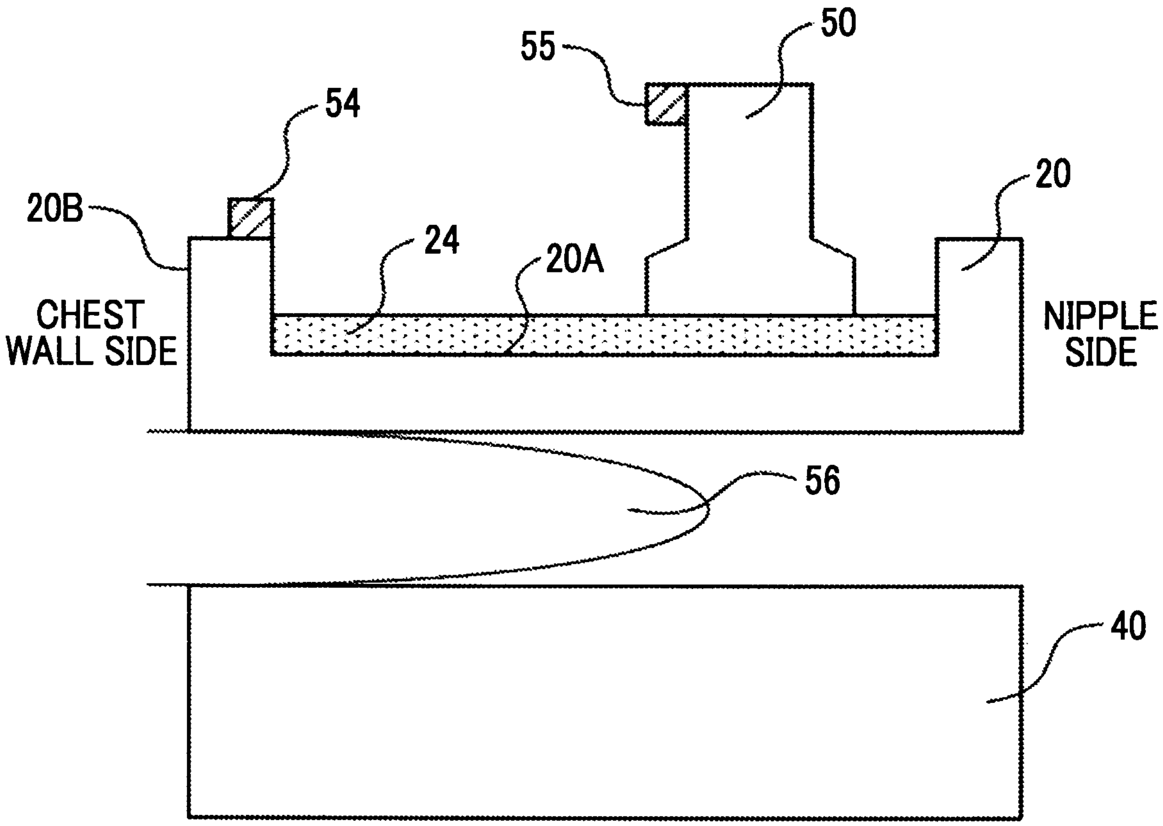
FIG. 3 is a side view showing a state in which a breast is compressed by a compression plate according to the first embodiment.

As shown in FIGS. 2 and 3, a magnetic generator 54 is provided on the chest wall side of the compression plate 20. In addition, a magnetic position sensor 55 is provided in the ultrasound probe 50. The magnetic position sensor 55 detects magnetism generated by the magnetic generator 54, whereby a distance in the Y axis direction from the side surface 20B of the compression plate 20 on the chest wall side to the ultrasound probe 50 can be detected.

As shown in FIG. 3, an acoustic matching material 24 is provided between the ultrasound probe 50 and the compression plate 20. As the acoustic matching material 24, for example, a gel sheet is used in which a gel-like or jelly-like acoustic matching material is accommodated. Here, the acoustic matching material is a member that fills a space between a bottom surface 20A of the compression plate 20 and the ultrasound probe 50 and is acoustically coupled to the breast 56 of the examinee. It is preferable that the acoustic matching material is a material having the acoustic impedance close to the acoustic impedance of the breast 56 of the examinee, the compression plate 20, and the ultrasound probe 50. By providing the acoustic matching material 24, a degree of contact between the compression plate 20 and the ultrasound probe 50 can be improved.

Figure 4A:
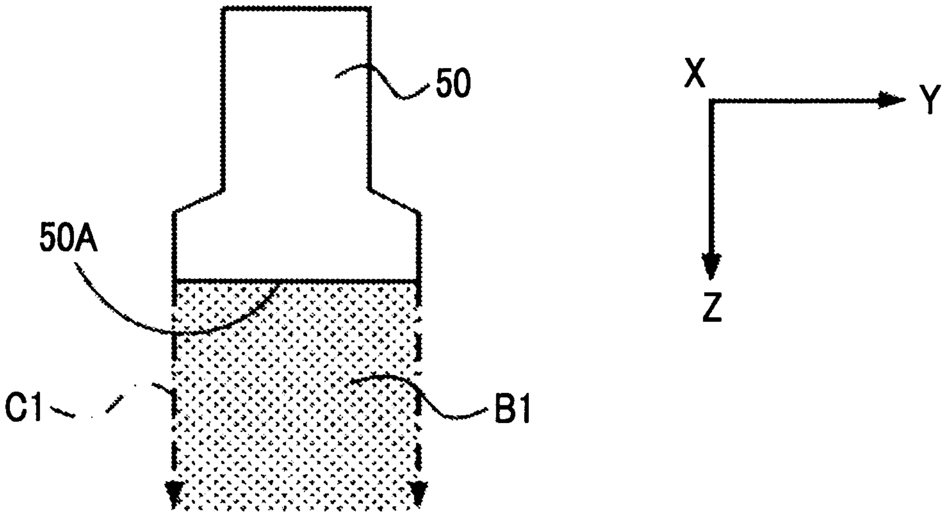
FIG. 4A is a diagram showing an ultrasound beam in a normal mode.

In addition, in a normal mode, as shown in FIG. 4A, the ultrasound probe 50 emits a wide ultrasound beam B1 along a normal direction C1 (Z axis direction in FIG. 4A) orthogonal to an emission surface 50A of the ultrasound probe 50.

Figure 4B:
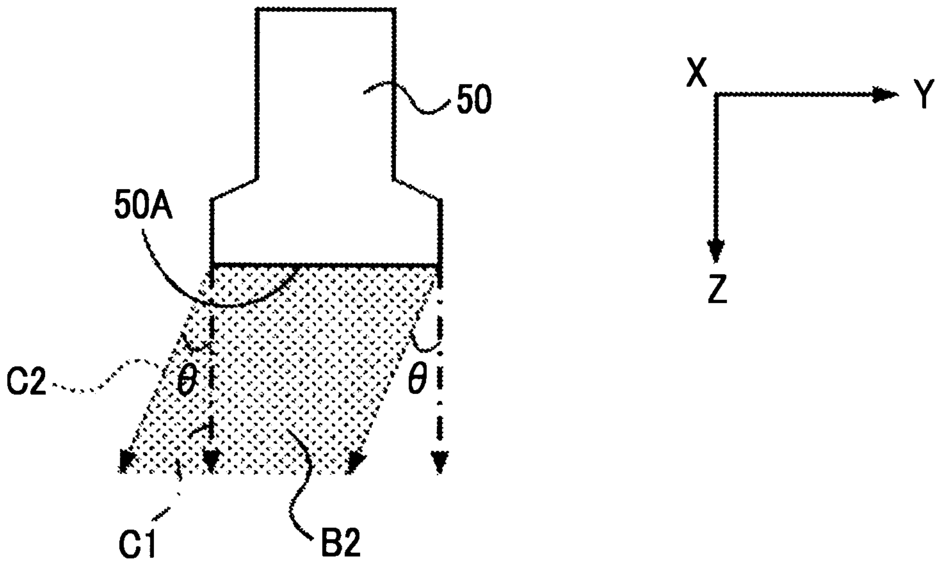
FIG. 4B is a diagram showing an ultrasound beam in a steer mode.

In addition, as shown in FIG. 4B, in a steer mode, the ultrasound probe 50 emits a wide ultrasound beam B2 along an inclination direction C2 inclined to a left side in FIG. 4B at an inclination angle θ with respect to the normal direction C1. It should be noted that, in the steer mode, it is also possible to emit a wide ultrasound beam along an inclination direction inclined to a right side in FIG. 4B at the inclination angle θ with respect to the normal direction C1.

Figure 4C:
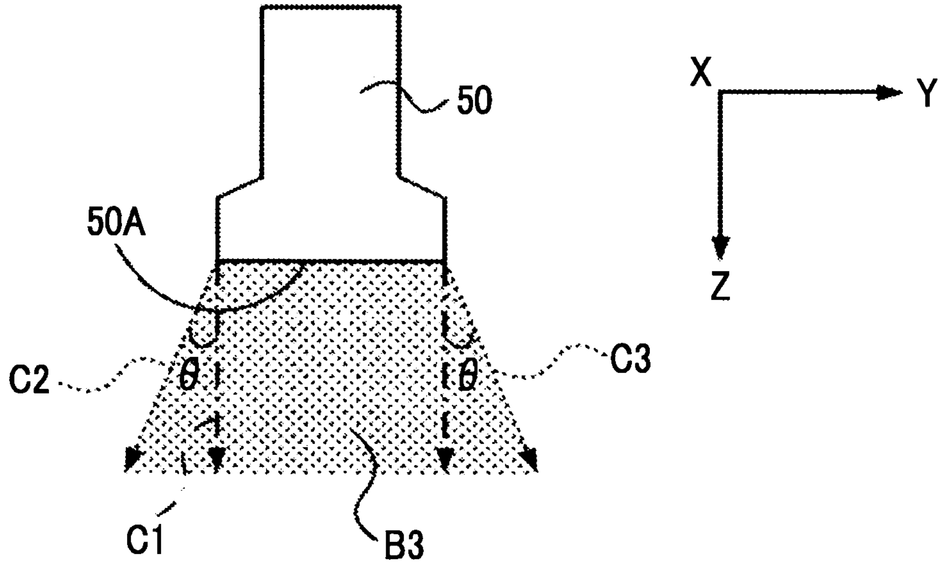
FIG. 4C is a diagram showing an ultrasound beam in a trapezoidal mode.

In addition, as shown in FIG. 4C, the ultrasound probe 50 emits an ultrasound beam B3 that spreads in a trapezoidal shape along the inclination direction C2 inclined to the left side in FIG. 4C at the inclination angle θ with respect to the normal direction C1 and a direction C3 inclined to the right side in FIG. 4C at the inclination angle θ in the trapezoidal mode.

Figure 5:
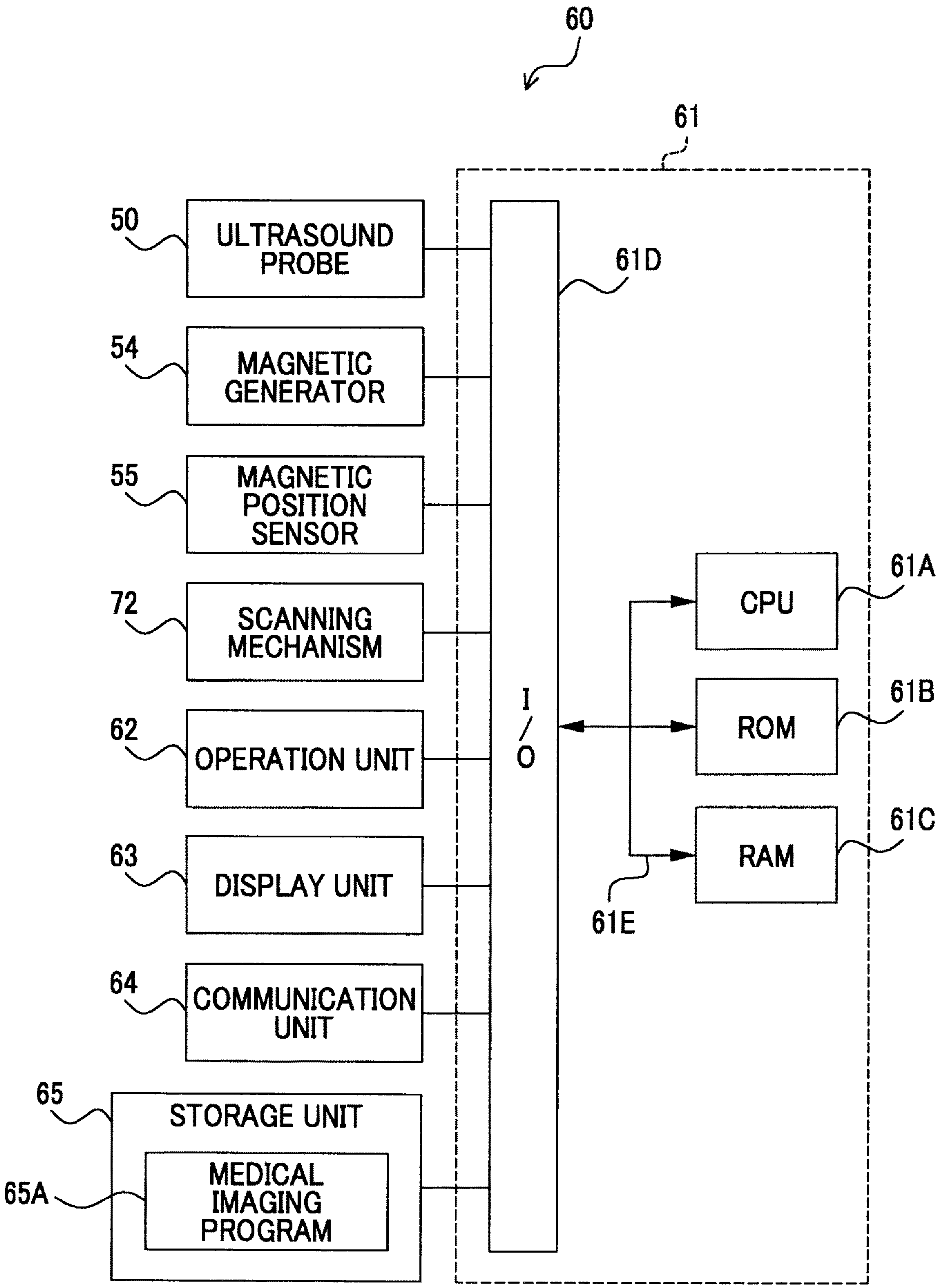
FIG. 5 is a block diagram showing a hardware configuration of a medical imaging apparatus according to the first embodiment.

FIG. 5 is a block diagram showing a hardware configuration of the medical imaging apparatus 60 according to the present embodiment. As shown in FIG. 5, the medical imaging apparatus 60 comprises a controller 61. The controller 61 is configured by a device including a general computer.

As shown in FIG. 5, the controller 61 comprises a central processing unit (CPU) 61A, a read only memory (ROM) 61B, a random access memory (RAM) 61C, and an input and output interface (I/O) 61D. The CPU 61A, the ROM 61B, the RAM 61C, and the I/O 61D are connected to each other via a bus 61E. The bus 61E includes a control bus, an address bus, and a data bus.

In addition, the ultrasound probe 50, the magnetic generator 54, the magnetic position sensor 55, an operation unit 62, a display unit 63, a communication unit 64, and a storage unit 65 are connected to the I/O 61D.

The operation unit 62 includes, for example, a mouse and a keyboard.

The display unit 63 is configured by, for example, a liquid crystal display.

The communication unit 64 is an interface for performing data communication with an external apparatus such as the mammography apparatus 10.

The storage unit 65 is configured by a nonvolatile external storage device such as a hard disk. As shown in FIG. 5, the storage unit 65 stores a medical imaging program 65A or the like.

The CPU 61A is an example of a processor. Here, the processor is a processor in a broad sense, and includes a general-purpose processor (for example, a CPU) or a dedicated processor (for example, a graphics processing unit (GPU), an application specific integrated circuit (ASIC), a field programmable gate array (FPGA), a programmable logic device, and the like).

It should be noted that the medical imaging program 65A may be realized by being stored in a nonvolatile non-transitory recording medium or being distributed via a network and being appropriately installed in the medical imaging apparatus 60.

Examples of the nonvolatile non-transitory recording medium include a compact disc read only memory (CD-ROM), an optical magnetic disk, a hard disk drive (HDD), a digital versatile disc read only memory (DVD-ROM), a flash memory, and a memory card.

Figure 6:
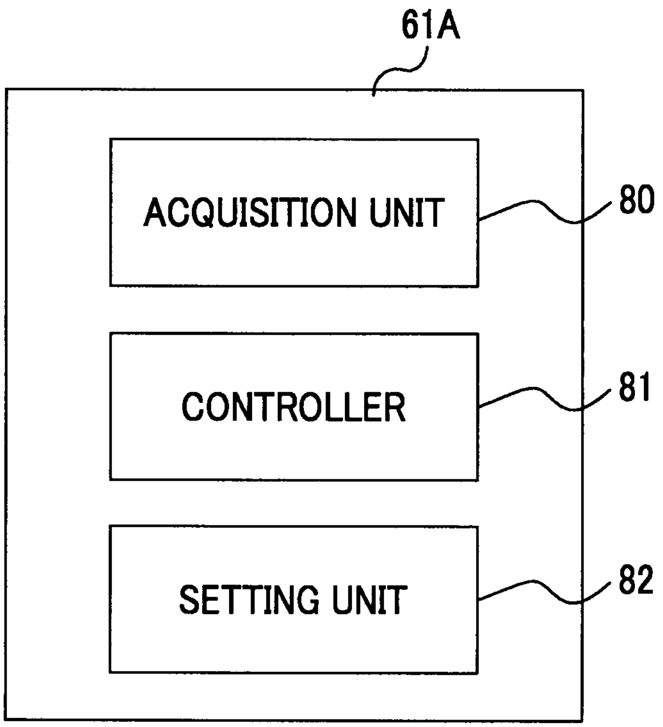
FIG. 6 is a block diagram showing a functional configuration of the medical imaging apparatus according to the first embodiment.

FIG. 6 is a block diagram showing a functional configuration of the CPU 61A of the medical imaging apparatus 60. As shown in FIG. 6, the CPU 61A comprises an acquisition unit 80, a controller 81, and a setting unit 82 as functional units.

The CPU 61A functions as the respective functional units shown in FIG. 6 by reading and executing the medical imaging program 65A stored in the storage unit 65.

The acquisition unit 80 acquires the position of the ultrasound probe 50 that emits the ultrasound beam to the breast 56 of the examinee, which is in a compressed state by the compression plate 20, from the magnetic position sensor 55. Specifically, the position of the ultrasound probe 50 in a direction orthogonal to the side surface 20B of the compression plate 20 on the chest wall side, that is, the Y axis direction is acquired from the magnetic position sensor 55.

The controller 81 performs control of switching an emission direction of the ultrasound beam to the chest wall side to the steer mode or the trapezoidal mode in a case in which the position of the ultrasound probe 50 acquired by the acquisition unit 80 is equal to or smaller than a predetermined distance from the side surface 20B and a predetermined switching condition is satisfied. That is, in a case in which the position of the ultrasound probe 50 acquired by the acquisition unit 80 is larger than the predetermined distance from the side surface 20B or the predetermined switching condition is not satisfied, the controller 81 controls the ultrasound probe 50 to emit the ultrasound beam B1 in the normal mode shown in FIG. 4A. On the other hand, in a case in which the position of the ultrasound probe 50 acquired by the acquisition unit 80 is equal to or smaller than the predetermined distance from the side surface 20B and the predetermined switching condition is satisfied, the ultrasound probe 50 is controlled to emit the ultrasound beam B2 in the steer mode shown in FIG. 4B or to emit the ultrasound beam B3 in the trapezoidal mode shown in FIG. 4C.

Figure 7:
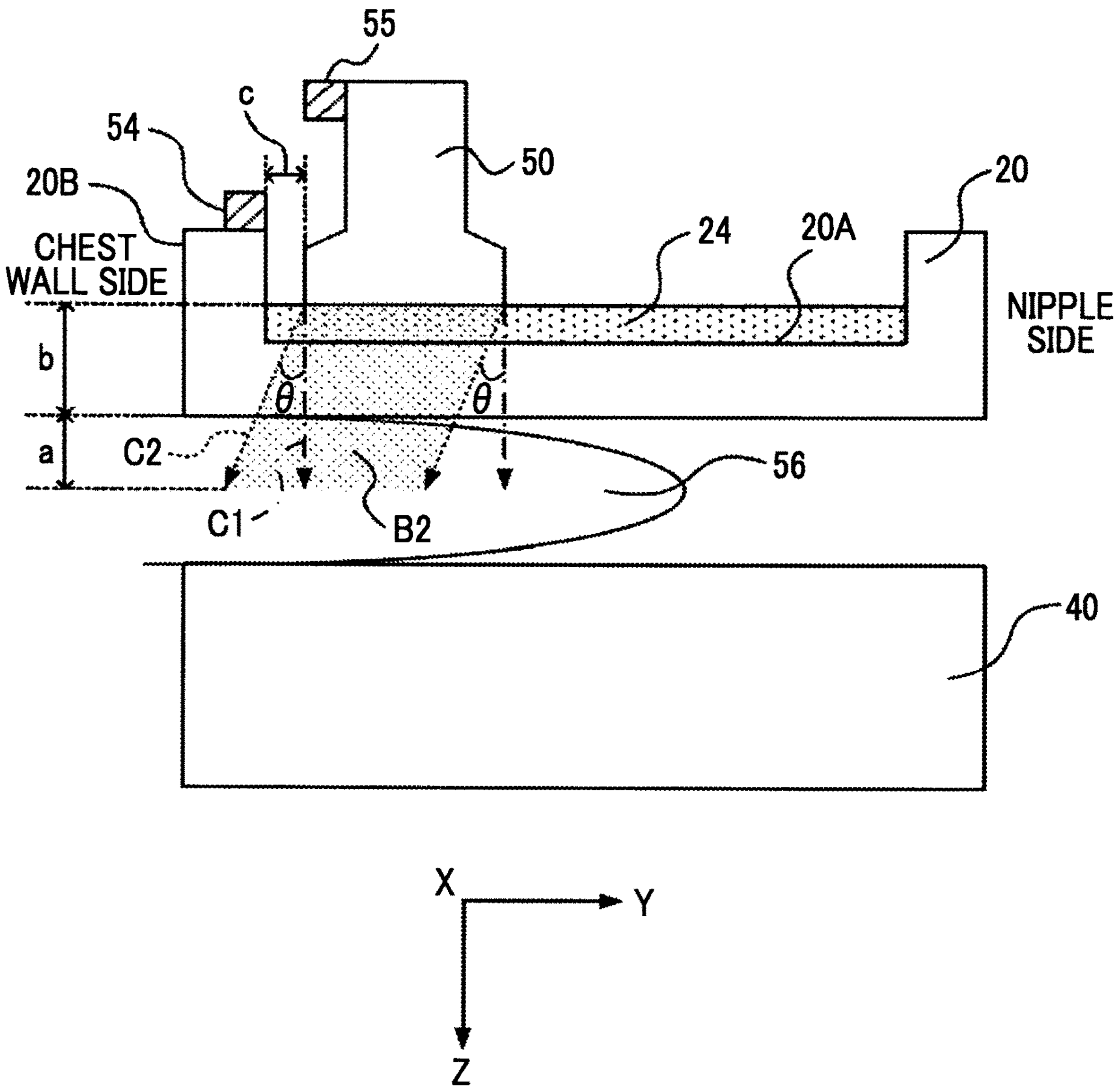
FIG. 7 is a diagram showing a state in which a chest wall side is imaged in the steer mode.

FIG. 7 shows an example in which the ultrasound beam B1 is emitted by switching to the steer mode in a case in which the ultrasound probe 50 is close to the side surface 20B on the chest wall side. In this way, by switching to the steer mode in a case in which the ultrasound probe 50 is close to the side surface 20B on the chest wall side and emitting the ultrasound beam B1, a region on the chest wall side of the breast 56, which is not irradiated in the normal mode, can be irradiated with the ultrasound beam B2, and the ultrasound image of a particularly shallow region on the chest wall side can be easily acquired. It should be noted that, in a case in which the imaging is performed in the trapezoidal mode, a deep region can be imaged over a wide range.

Here, in a case in which the predetermined distance is denoted by D, the inclination angle of the ultrasound beam emitted in the steer mode or the trapezoidal mode is denoted by θ, a depth of the breast 56 to be observed is denoted by a, and a distance between the ultrasound probe 50 and the compression plate 20, that is, a distance in the Z axis direction is denoted by b, as shown in FIG. 7, the predetermined distance D may be a distance represented by $\tan\theta \times (a+b)$. In this case, as shown in FIG. 7, in a case in which a distance c satisfies $c \leq D$ in which a distance from the side surface 20B on the chest wall side to the ultrasound probe 50 is denoted by c, and the predetermined switching condition is satisfied, the switching is performed to the steer mode or the trapezoidal mode. In a case in which $c > D$, even in a case in which the ultrasound beam is emitted by switching to the steer mode or the trapezoidal mode, the irradiated region is a region that can be irradiated even in the normal mode, so that it is not necessary to switch the emission mode.

It should be noted that the presence of a tumor near the skin ($a=0$) of the breast 56 is rare, and thus, for example, in a case in which a is 30 mm, b is 10 mm, and θ is 15 degrees, D is approximately 10.7 mm.

In addition, in a case in which a thickness of the acoustic matching material 24 is too thin, the effect as the acoustic matching material cannot be expected, and in a case in which the thickness of the acoustic matching material 24 is too thick, an artifact may occur in the ultrasound image. Therefore, it is preferable that the thickness of the acoustic matching material 24 is 1 mm or larger and 10 mm or smaller.

Figure 8:
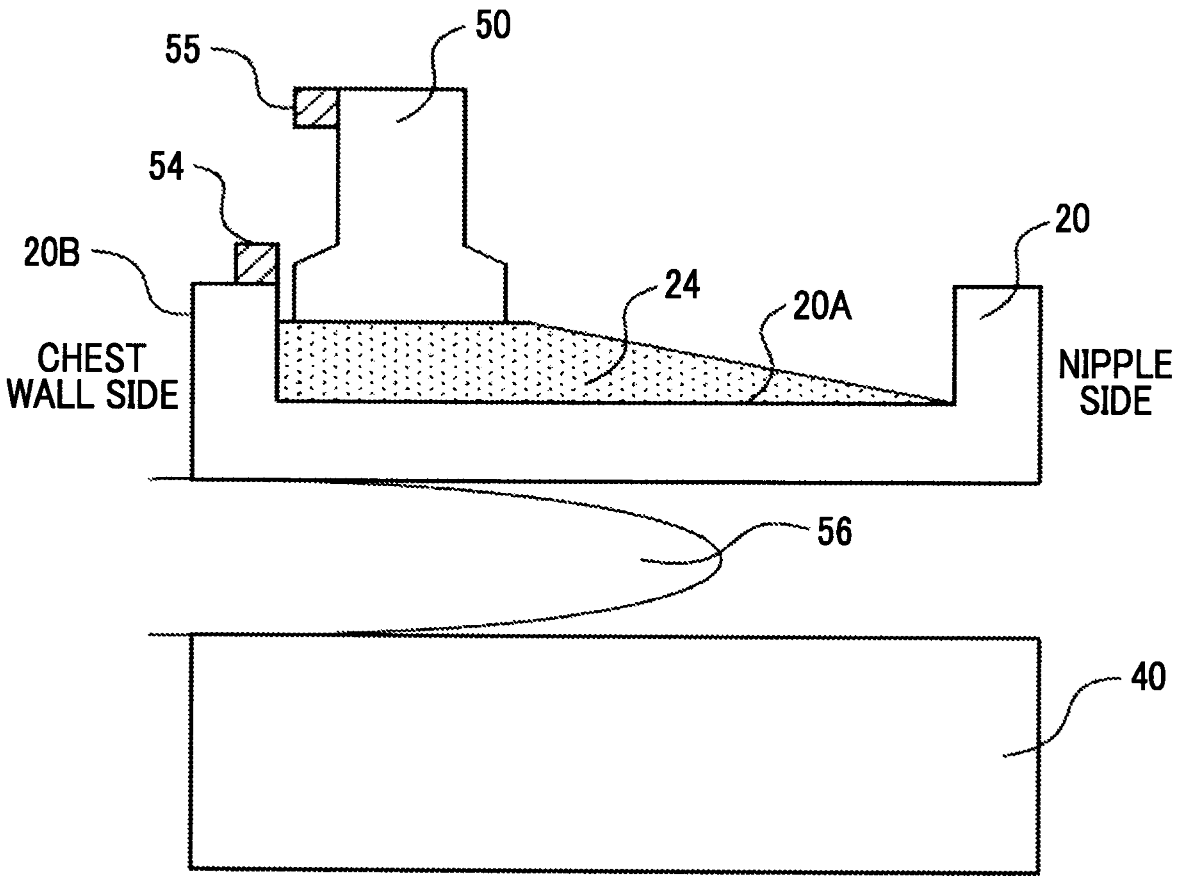
FIG. 8 is a diagram showing a modification example of an acoustic matching material.

In addition, as shown in FIG. 8, a configuration may be adopted in which the thickness of the acoustic matching material 24 is larger as a distance to the chest wall is smaller. As a result, in a case of performing the imaging in the steer mode or the trapezoidal mode, a region on the chest wall side that is not imaged can be reduced.

Figure 9:
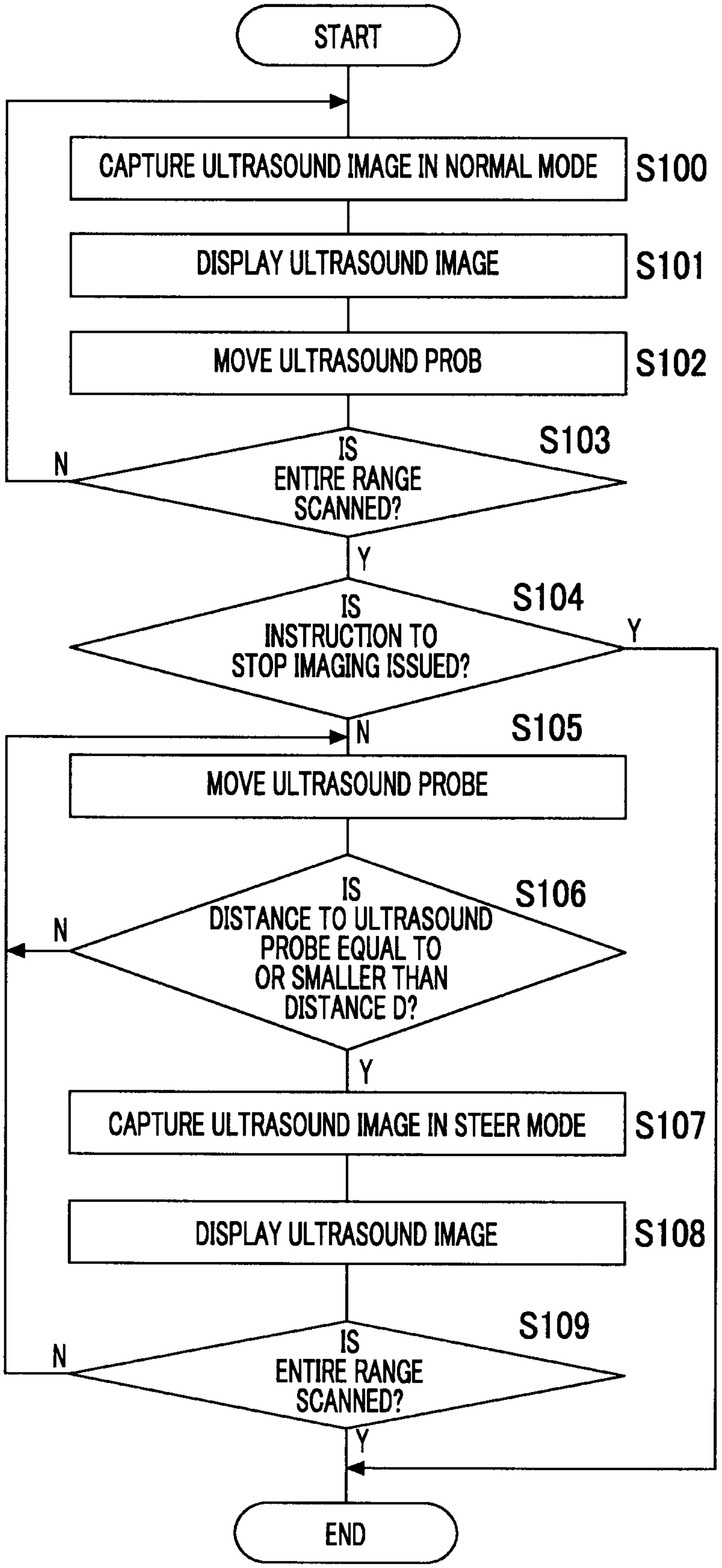
FIG. 9 is a flowchart showing medical imaging processing according to the first embodiment.

Next, medical imaging processing executed by the CPU 61A will be described with reference to a flowchart shown in FIG. 9. It should be noted that the processing shown in FIG. 9 is executed after the mammography apparatus 10 captures the radiation image of the breast 56 compressed by the compression plate 20.

In step S100, the CPU 61A instructs the ultrasound probe 50 to capture the ultrasound image in the normal mode. As a result, as shown in FIG. 4A, the ultrasound probe 50 emits the wide ultrasound beam B1 along the normal direction C1 orthogonal to the emission surface 50A and captures the ultrasound image.

In step S101, the CPU 61A displays the ultrasound image, which is captured in step S100, on the display unit 63.

In step S102, the CPU 61A controls the scanning mechanism 72 such that the ultrasound probe 50 on the chest wall side moves toward a nipple side along the route R.

In step S103, the CPU 61A determines whether or not the entire range is scanned. That is, it is determined whether or not the ultrasound probe 50 is moved over the entire range along the route R. Then, in a case in which the ultrasound probe 50 does not scan the entire range, the processing proceeds to step S100. On the other hand, in a case in which the ultrasound probe 50 scans the entire range, the processing proceeds to step S104. As a result, the capturing of the ultrasound image in the normal mode ends. An operator views the ultrasound image displayed on the display unit 63 to determine whether or not the imaging may be stopped and end, and in a case in which it is determined that the imaging may be stopped, the operator operates the operation unit 62 to issue an instruction to stop the imaging. On the other hand, in a case in which the operator views the ultrasound image displayed on the display unit 63 and determines that the ultrasound image on the chest wall side needs to be captured, the operator does not issue an instruction to stop the imaging and continues the imaging.

Therefore, in step S104, the CPU 61A determines whether or not the instruction to stop the imaging is issued within a certain period of time. That is, as the switching condition of the imaging mode, it is determined whether or not the instruction to stop the imaging of the ultrasound image via the ultrasound probe 50 is received. Then, in a case in which the instruction to stop the imaging is issued within a certain period of time, the present routine ends. On the other hand, in a case in which the instruction to stop the imaging is not issued within a certain period of time, the processing proceeds to step S105.

In step S105, the CPU 61A controls the scanning mechanism 72 such that the ultrasound probe 50 on the nipple side moves toward the chest wall side along the route R.

In step S106, the CPU 61A acquires the position of the ultrasound probe 50 from the magnetic position sensor 55, to determine whether or not the distance c in the Y axis direction from the side surface 20B on the chest wall side to the ultrasound probe 50 is equal to or smaller than the predetermined distance D. Then, in a case in which the distance c is equal to or smaller than the distance D, that is, in a case in which the position of the ultrasound probe 50 is close to the chest wall side, the processing proceeds to step S107. On the other hand, in a case in which the distance c is larger than the distance D, that is, in a case in which the position of the ultrasound probe 50 is not close to the chest wall side, the processing proceeds to step S105.

In step S107, the CPU 61A instructs the ultrasound probe 50 to capture the ultrasound image in the steer mode. As a result, as shown in FIG. 4B, the ultrasound probe 50 emits the wide ultrasound beam B2 along the inclination direction C2 in which the ultrasound beam B2 is inclined at the inclination angle θ with respect to the normal direction C1. It should be noted that the ultrasound probe 50 may be instructed to capture the ultrasound image in the trapezoidal mode as shown in FIG. 4C. As a result, as shown in FIG. 7, the chest wall side, which is not irradiated in the normal mode, is irradiated with the ultrasound beam B2.

In step S108, the CPU 61A displays the ultrasound image, which is captured in step S107, on the display unit 63.

In step S109, the CPU 61A determines whether or not the ultrasound probe 50 performs the scanning over the entire range along the route R. Then, in a case in which the ultrasound probe 50 does not perform the scanning over the entire range along the route R, the processing proceeds to step S105. On the other hand, in a case in which the ultrasound probe 50 performs the scanning over the entire range along the route R, the present routine ends.

As described above, in the present embodiment, in a case in which the ultrasound probe 50 approaches the chest wall side, the imaging mode is switched from the normal mode to the steer mode to capture the ultrasound image. As a result, the acquisition of the ultrasound image on the chest wall side is facilitated.

It should be noted that, in a case in which the ultrasound image is displayed on the display unit 63 in steps S101 and S108, a first imaging region imaged in a state in which the emission direction of the ultrasound beam is the normal direction C1 as shown in FIG. 4A, and a second imaging region imaged in the steer mode or the trapezoidal mode in which the emission direction of the ultrasound beam is inclined as shown in FIGS. 4B and 4C are displayed in a distinguishable manner on the display unit 63, and the captured ultrasound image may be displayed on the display unit 63.

Figure 10:
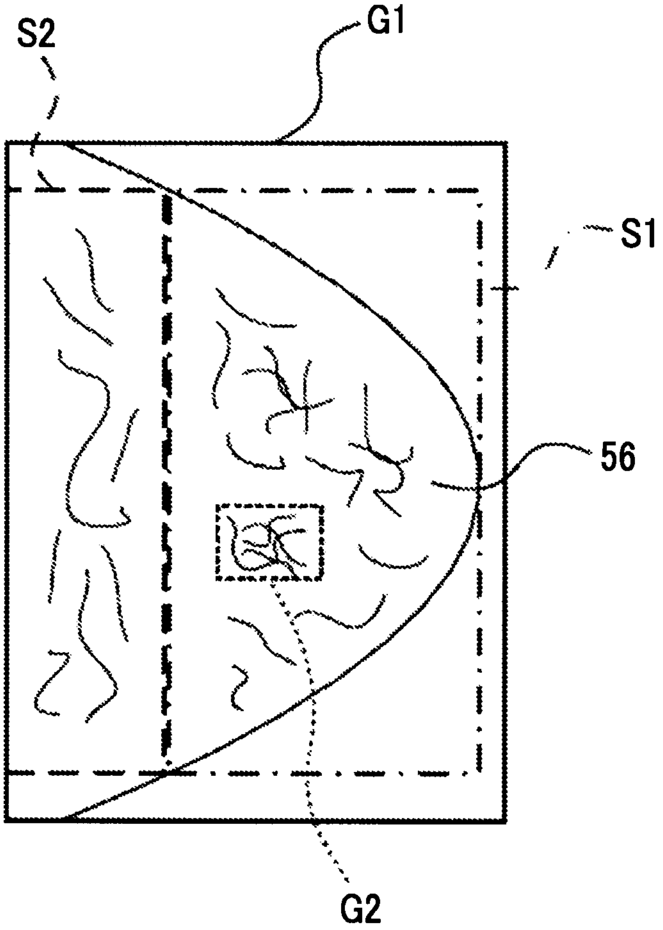
FIG. 10 is a top view schematically showing an example of a guide member according to the first embodiment.

For example, as shown in FIG. 10, a radiation image G1 captured by the mammography apparatus 10 is acquired, a first imaging region S1 captured in the normal mode and a second imaging region S2 captured in the steer mode or the trapezoidal mode are displayed on the acquired radiation image G1 in a distinguishable manner on the display unit 63, and a captured ultrasound image G2 is displayed on the display unit 63. As a result, it is possible to easily understand whether or not the captured ultrasound image is the ultrasound image captured in the first imaging region S1 or the ultrasound image captured in the steer mode or the trapezoidal mode.

Second Embodiment

Hereinafter, a second embodiment will be described. It should be noted that the same parts as those in the first embodiment are denoted by the same reference numerals, and the detailed description thereof will be omitted.

Although, in the first embodiment, a case has been described in which the imaging ends in a case in which the operator intervenes and issues the instruction to stop the imaging after the ultrasound image is captured in the normal mode, in the present embodiment, a case will be described in which the operator does not intervene.

In the second embodiment, a configuration of the medical imaging system 100 is the same as the configuration in the first embodiment, and thus the description thereof will be omitted.

Figure 11:
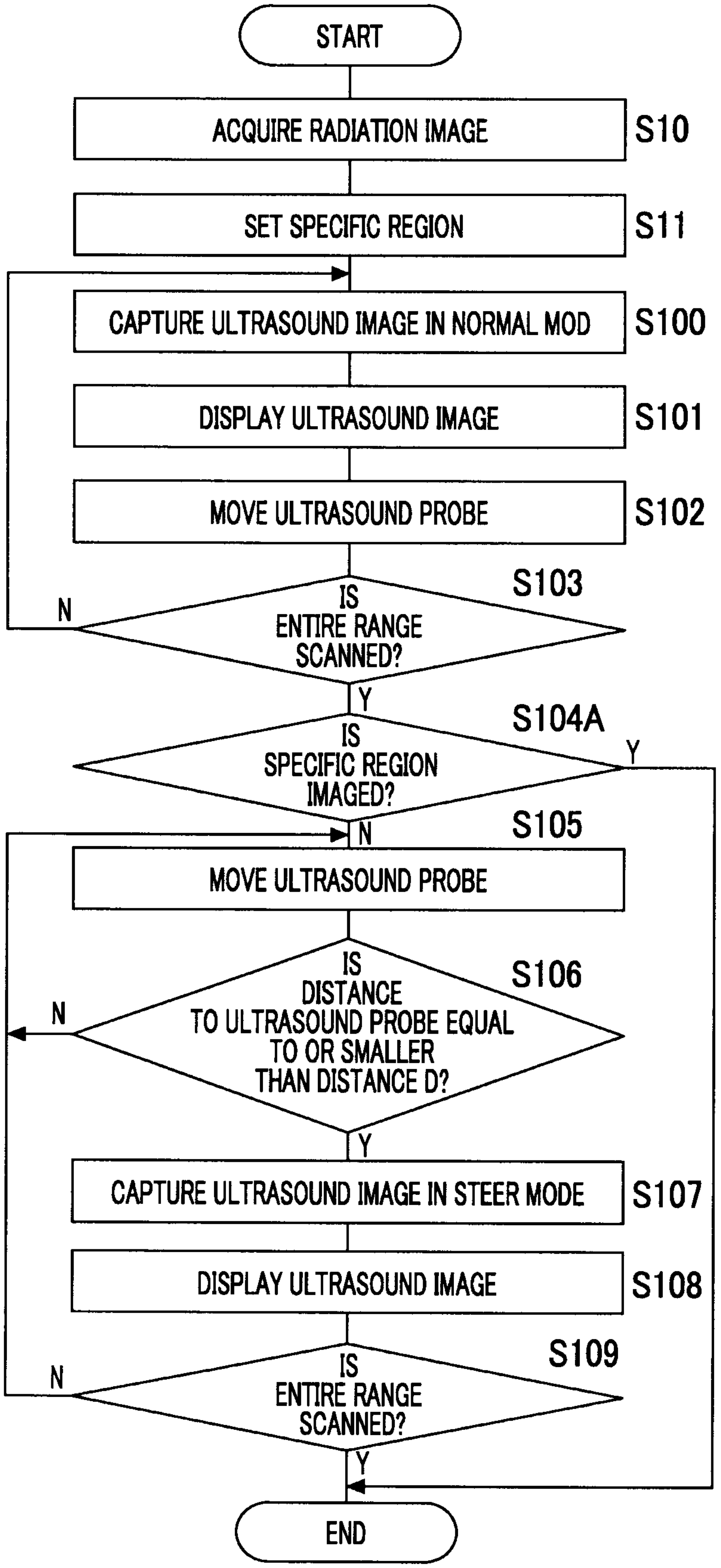
FIG. 11 is a flowchart showing medical imaging processing according to a second embodiment.

Next, medical imaging processing executed by the CPU 61A will be described with reference to a flowchart shown in FIG. 11. It should be noted that the processing shown in FIG. 11 is executed after the mammography apparatus 10 captures the radiation image of the breast 56 compressed by the compression plate 20.

In step S10, the CPU 61A acquires the radiation image captured by the mammography apparatus 10.

In step S11, the CPU 61A specifies a region in which the tumor or the like is suspected, based on the radiation image acquired in step S10, for example, by a known image analysis method, and sets the specified region as a specific region to be irradiated with the ultrasound beam.

Since steps S100 to S103 are the same as in the processing of FIG. 9, the description thereof will be omitted.

In step S104A, the CPU 61A determines whether or not the capturing of the ultrasound image is performed for the specific region set in step S11. That is, it is determined whether or not the specific region is a region that is on the chest wall side and cannot be imaged in the normal mode. In a case in which the capturing of the ultrasound image is performed for the specific region, the present routine ends. On the other hand, as the switching condition of the imaging mode, in a case in which the capturing of the ultrasound image is not performed for the specific region, the processing proceeds to step S105.

Since steps S105 to S109 are the same as in the processing of FIG. 9, the description thereof will be omitted.

As described above, in the present embodiment, the region in which the tumor or the like is suspected is specified based on the radiation image, and in a case in which the specified region is on the chest wall side, the processing of switching from the normal mode to the steer mode or the trapezoidal mode and capturing the ultrasound image can be automatically performed.

Third Embodiment

Hereinafter, a third embodiment will be described. It should be noted that the same parts as those in the first embodiment are denoted by the same reference numerals, and the detailed description thereof will be omitted.

Although, in the first embodiment, a case has been described in which the ultrasound image is captured by automatically moving the ultrasound probe 50, in the present embodiment, a case will be described in which the ultrasound image is captured by moving the ultrasound probe 50 manually by the operator.

The medical imaging system 100 according to the third embodiment has a configuration in which the compression plate 20 comprises a guide member that guides the ultrasound probe 50 such that the longitudinal direction of the ultrasound probe 50 is a direction orthogonal to the chest wall, instead of the scanning mechanism 72, and the magnetic generator 54 and the magnetic position sensor 55 are omitted.

Figure 12:
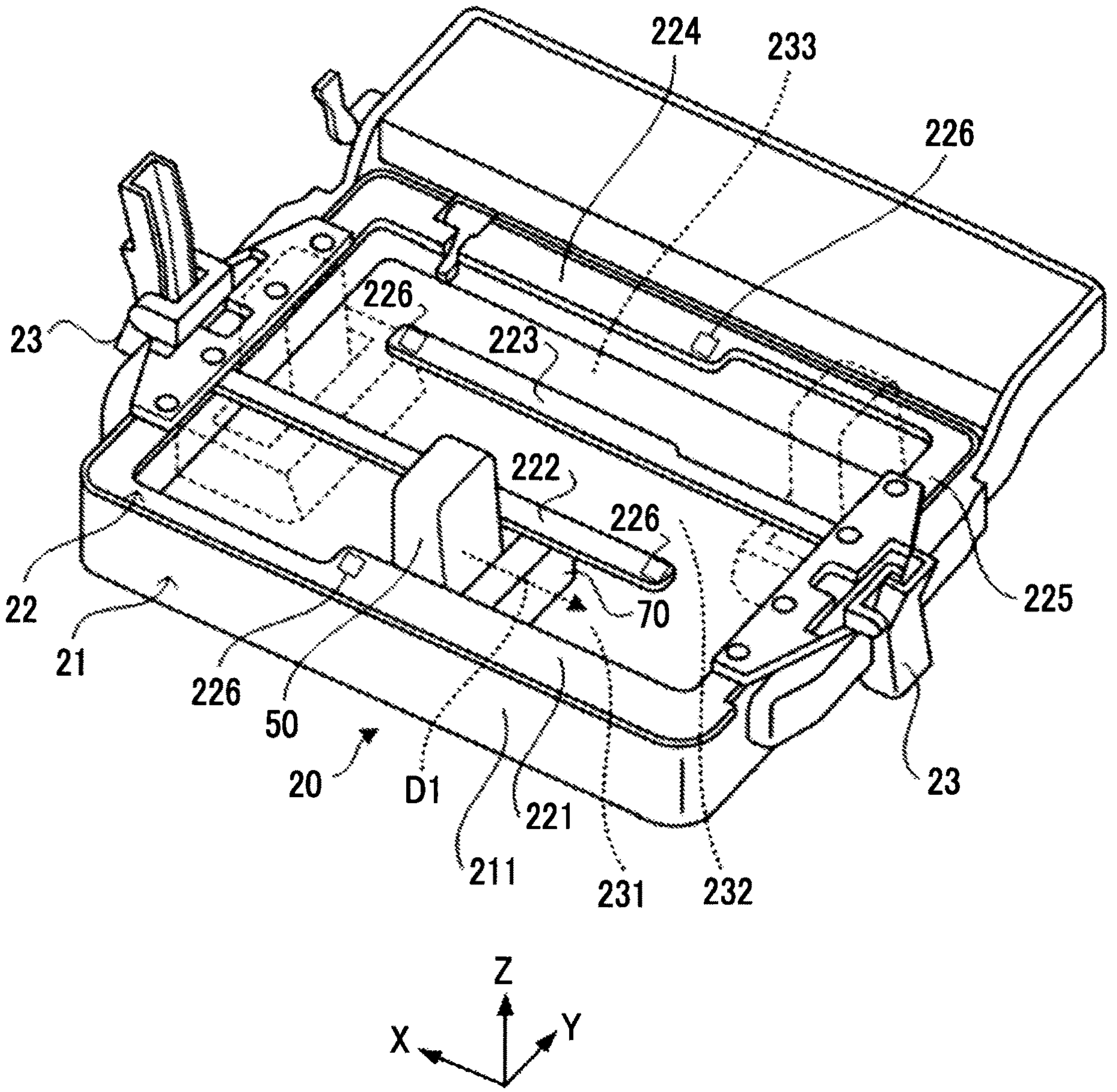
FIG. 12 is a perspective view schematically showing an example of a compression plate according to a third embodiment.

FIG. 12 is a perspective view schematically showing an example of the compression plate 20 according to the third embodiment.

As shown in FIG. 12, the compression plate 20 according to the present embodiment comprises a body part 21, a guide member 22, and a locking mechanism 23. The body part 21 is a box-shaped member with an open top and has a chest wall surface 211. The chest wall surface 211 is a surface facing a chest wall of the examinee. The guide member 22 is a member provided in the body part 21. The guide member 22 guides the ultrasound probe 50 along a scanning direction D1 of the ultrasound probe 50.

The locking mechanism 23 attachably and detachably fixes the guide member 22 to the body part 21. The locking mechanism 23 is provided on the guide member 22 as an example, but may be provided on the body part 21. The mammography can be performed in a state in which the guide member 22 is removed from the body part 21 in a case of the mammography, and the ultrasonography can be performed in a state in which the guide member 22 is attached to the body part 21 in a case of the ultrasonography. In addition, by comprising the locking mechanism 23, it is possible to prevent the guide member 22 from falling off from the body part 21 even in a case in which the compression plate 20 is inclined.

The guide member 22 includes a first guide part 221, a second guide part 222, a third guide part 223, a fourth guide part 224, a frame part 225, and a position detection sensor 226. The first guide part 221, the second guide part 222, the third guide part 223, and the fourth guide part 224 are provided in a direction along the chest wall surface 211 of the body part 21 as an example, but may be provided in a direction intersecting the chest wall surface 211 of the body part 21. A cross-sectional shape of each of the first guide part 221, the second guide part 222, the third guide part 223, and the fourth guide part 224 is not particularly limited, but need only be, for example, a circular shape, an elliptical shape, a triangular shape, or a rectangular shape.

The frame part 225 is a frame-like part provided along the periphery of the body part 21. The first guide part 221 is a part that protrudes in a direction of the second guide part 222 from the frame part 225. The second guide part 222 is a part that extends from one end of the frame part 225 toward the other end of the frame part 225 facing the one end. The third guide part 223 is a part that extends from the other end of the frame part 225 toward one end of the frame part 225 facing the other end. The fourth guide part 224 is a part that protrudes in a direction of the third guide part 223 from the frame part 225.

The first guide part 221 and the second guide part 222 guide the ultrasound probe 50 along a first scanning path 231. The second guide part 222 and the third guide part 223 guide the ultrasound probe 50 along a second scanning path 232. The third guide part 223 and the fourth guide part 224 guide the ultrasound probe 50 along a third scanning path 233.

The first guide part 221 and the second guide part 222 are disposed such that effective image regions of the ultrasound probe 50 partially overlap each other in a case in which scanning using the ultrasound probe 50 is performed along the first scanning path 231 and the second scanning path 232. Similarly, the second guide part 222 and the third guide part 223 are disposed such that effective image regions of the ultrasound probe 50 partially overlap each other in a case in which scanning using the ultrasound probe 50 is performed along the second scanning path 232 and the third scanning path 233. Since the effective image regions of the ultrasound probe 50 can partially overlap each other, scanning omission of the ultrasound probe 50 can be suppressed.

Each of the first guide part 221, the second guide part 222, the third guide part 223, and the fourth guide part 224 is provided with the position detection sensor 226. The position detection sensor 226 is a sensor for detecting the position of the ultrasound probe 50, and various sensors such as an optical sensor, an ultrasound sensor, and a magnetic sensor are used as the position detection sensor 226. The position detection sensor 226 detects whether the ultrasound probe 50 is located on the first scanning path 231, the second scanning path 232, or the third scanning path 233. A detection result of the position detection sensor 226 is displayed on, for example, the display unit 63 of the medical imaging apparatus 60, and the user can understand the position of the ultrasound probe 50 while viewing the ultrasound image without looking at a hand gripping the ultrasound probe 50. However, the number and the attachment locations of the position detection sensors 226 are not limited to the example of FIG. 12, and the position detection sensors 226 need only be at a location at which the position of the ultrasound probe 50 can be appropriately detected.

It should be noted that, in the example of FIG. 12, a distal end part of the ultrasound probe 50 is held by a holding member 70, and the scanning using the ultrasound probe 50 is performed in a state in which the distal end part is held by the holding member 70. The holding member 70 is a member that holds the distal end part of the ultrasound probe 50 such that the holding member 70 surrounds the periphery of the distal end part of the ultrasound probe 50, and a posture of the ultrasound probe 50 can be stabilized by providing the holding member 70.

In the example of FIG. 12, the first guide part 221 and the fourth guide part 224 are provided on the guide member 22 side, but the first guide part 221 and the fourth guide part 224 may be provided on the body part 21 side. In this case, the second guide part 222 is replaced with the first guide part 221, and the third guide part 223 is replaced with the second guide part 222.

In the example of FIG. 12, four guide parts are provided, but the guide parts are not limited to four. The number of the guide parts need only be two or more, and may be five or more depending on the shape of the ultrasound probe 50, the size of the compression plate 20, and the like.

Figure 13:
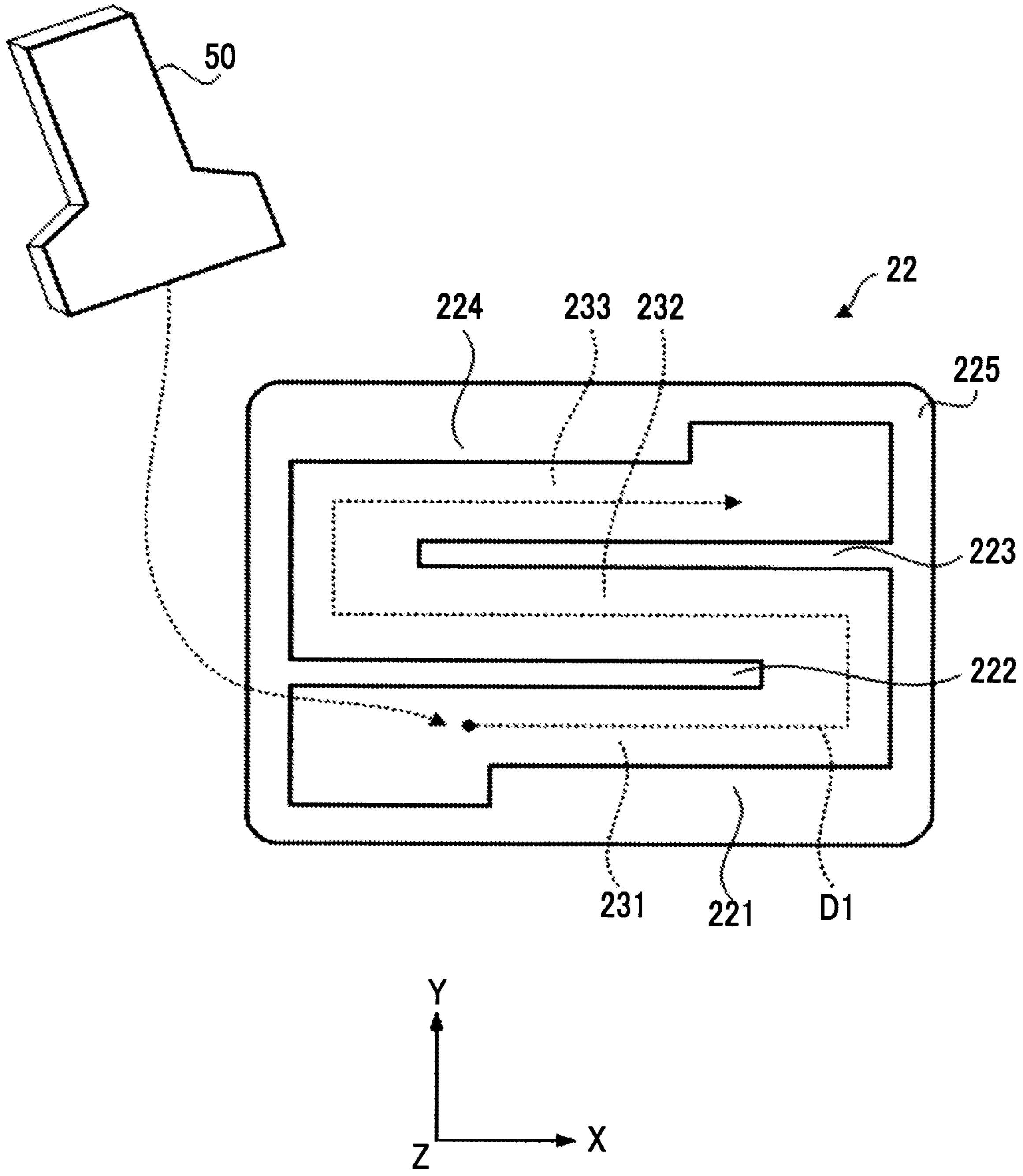
FIG. 13 is a top view schematically showing an example of a guide member according to the third embodiment.

FIG. 13 is a top view schematically showing an example of the guide member 22 according to the third embodiment.

As described above, the guide member 22 shown in FIG. 13 includes the first guide part 221, the second guide part 222, the third guide part 223, the fourth guide part 224, and the frame part 225. The second guide part 222 extends from one end of the frame part 225 toward the other end of the frame part 225 facing the one end, and the third guide part 223 extends from the other end of the frame part 225 toward one end of the frame part 225 facing the other end. That is, the second guide part 222 and the third guide part 223 are disposed in a staggered manner. The second guide part 222 and the third guide part 223 are disposed in a staggered manner, so that the scanning using the ultrasound probe 50 can be performed in a zigzag manner. Here, the term "zigzag" refers to a state in which a straight line is bent in a Z shape.

Figure 14:
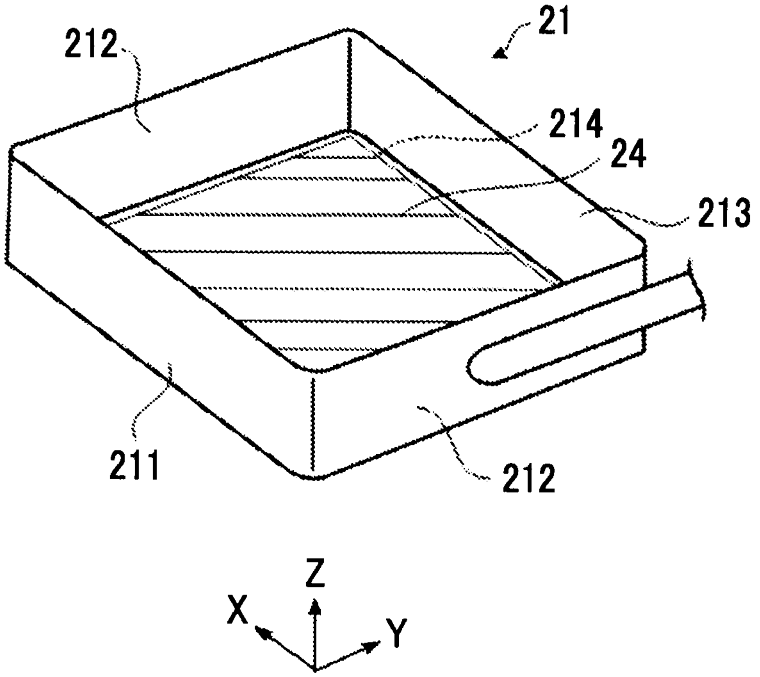
FIG. 14 is a perspective view schematically showing an example of a body part according to the third embodiment.

FIG. 14 is a perspective view schematically showing an example of the body part 21 according to the present embodiment.

The body part 21 shown in FIG. 14 includes a chest wall surface 211, two side surfaces 212, a rear surface 213, and a lower surface 214. The chest wall surface 211, the two side surfaces 212, and the rear surface 213 are disposed to surround the lower surface 214. The guide member 22 comprises an acoustic matching material 24 that is interposed between the ultrasound probe 50 and the examinee.

The acoustic matching material 24 is, for example, provided on the entire lower surface 214 of the body part 21.

Figure 15:
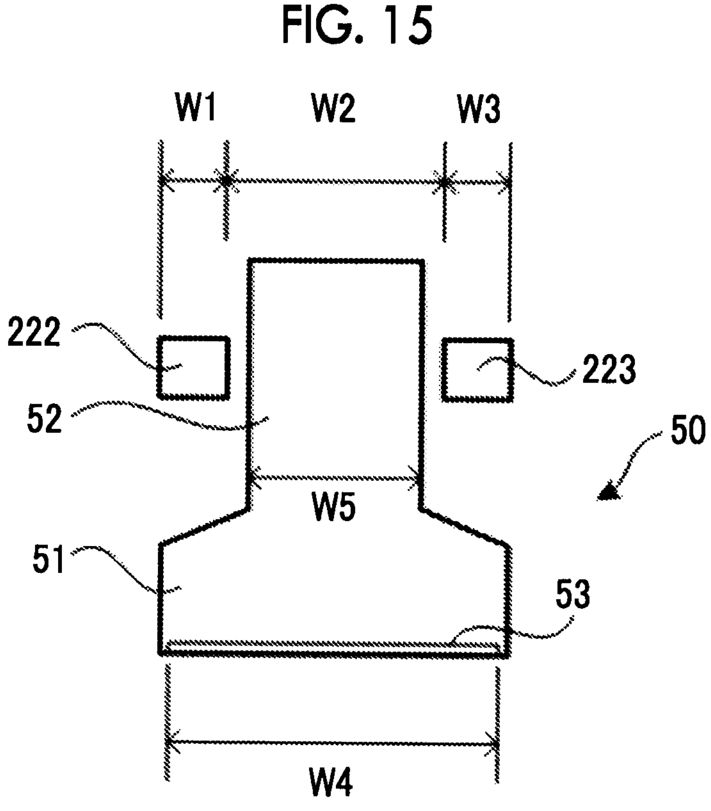
FIG. 15 is a diagram showing an example of a positional relationship between an ultrasound probe, a second guide part, and a third guide part according to the third embodiment.

FIG. 15 is a diagram showing an example of a positional relationship between the ultrasound probe 50, the second guide part 222, and the third guide part 223 according to the present embodiment.

The ultrasound probe 50 shown in FIG. 15 includes a transceiver unit 51 and a gripping part 52. The transceiver unit 51 is a unit that transmits and receives the ultrasound. The gripping part 52 is a part that is continuous with the transceiver unit 51 and is gripped by the user. A width W5 of the gripping part 52 is smaller than a width W4 of an effective image region 53 of the transceiver unit 51.

Here, in a case in which a width of the second guide part 222 is denoted by W1, a distance between the second guide part 222 and the third guide part 223 is denoted by W2, a width of the third guide part 223 is denoted by W3, and a width of the effective image region 53 of the ultrasound probe 50 is denoted by W4, the following relationship represented by Expression (1) is satisfied.

$$W4>W1/2+W2+W3/2 \qquad (1)$$

By disposing the second guide part 222 and the third guide part 223 such that Expression (1) is satisfied, the effective image regions 53 of the ultrasound probe 50 can partially overlap each other in a case in which the scanning using the ultrasound probe 50 is performed along the first scanning path 231 and the second scanning path 232.

It should be noted that, in the present embodiment, in a case in which the ultrasound probe 50 is present on the first scanning path 231, the distance c in the Y axis direction from the side surface 20B on the chest wall side to the ultrasound probe 50 is equal to or smaller than the predetermined distance D. In addition, in a case in which the ultrasound probe 50 is present on the second scanning path 232 or the third scanning path 233, the distance c is set to be larger than the predetermined distance D.

Figure 16:
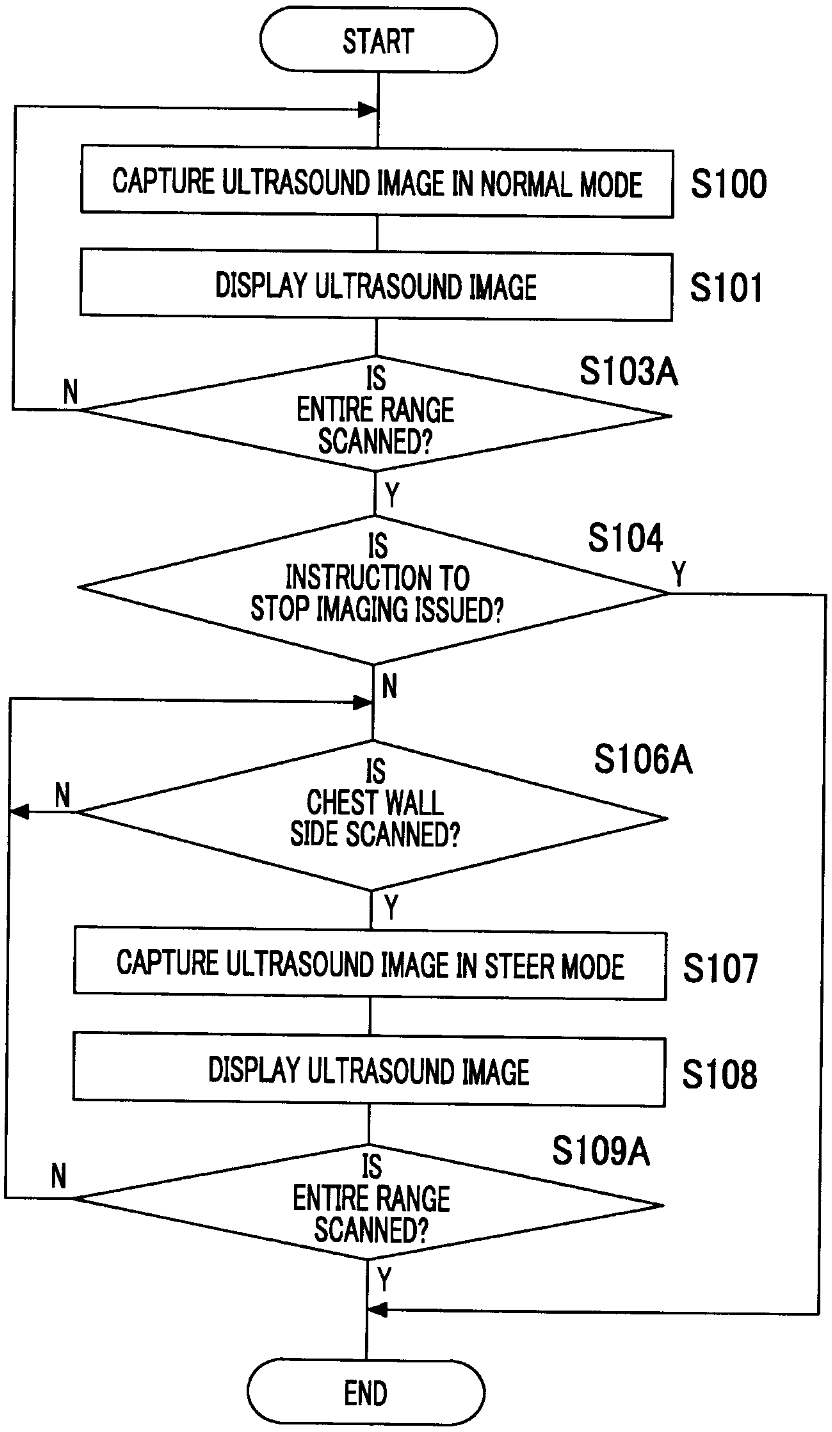
FIG. 16 is a flowchart showing medical imaging processing according to the third embodiment.

Next, medical imaging processing executed by the CPU 61A will be described with reference to a flowchart shown in FIG. 16.

The operator performs the scanning using the ultrasound probe 50, for example, along the first scanning path 231, the second scanning path 232, and the third scanning path 233.

Since steps S100 and S101 are the same as in the processing of FIG. 9, the description thereof will be omitted.

In step S103A, the CPU 61A determines whether or not the entire range is scanned. In the present embodiment, since the operator manually performs the scanning using the ultrasound probe 50, the operator operates the operation unit 62 to perform input indicating that the scanning of the entire range ends after the entire range is scanned.

Therefore, in step S103A, the CPU 61A determines whether or not the input indicating that the scanning over the entire range ends by the operation of the operator is performed. Then, in a case in which the input indicating that the scanning over the entire range ends is performed, the processing proceeds to step S104, and in a case in which the input indicating that the scanning over the entire range ends is not performed, the processing proceeds to step S100.

Here, as in the first embodiment, the operator views the ultrasound image displayed on the display unit 63 to determine whether or not the imaging may be stopped and end, and in a case in which it is determined that the imaging may be stopped, the operator operates the operation unit 62 to issue an instruction to stop the imaging. On the other hand, in a case in which the operator views the ultrasound image displayed on the display unit 63 and determines that the ultrasound image on the chest wall side needs to be captured, the operator does not issue an instruction to stop the imaging and continues the imaging.

In step S104, the CPU 61A determines whether or not the instruction to stop the imaging is issued within a certain period of time. That is, as the switching condition of the imaging mode, it is determined whether or not the instruction to stop the imaging of the ultrasound image via the ultrasound probe 50 is received. Then, in a case in which the instruction to stop the imaging is issued within a certain period of time, the present routine ends. On the other hand, in a case in which the instruction to stop the imaging is not issued within a certain period of time, the processing proceeds to step S106A.

In a case in which the operator does not issue the instruction to stop the imaging, the operator starts the scanning using the ultrasound probe 50 again.

In step S106A, the CPU 61A is determined whether or not the scanning is performed on the chest wall side, specifically, whether or not the ultrasound probe 50 performs the scanning on the first scanning path 231. Then, in a case in which the chest wall side is scanned, that is, in a case in which the distance c is equal to or smaller than the predetermined distance D, the processing proceeds to step S107. On the other hand, in a case in which the chest wall side is not scanned, that is, in a case in which the ultrasound probe 50 performs the scanning on the second scanning path 232 or the third scanning path 233 and the distance c is larger than the predetermined distance D, the processing waits until the ultrasound probe 50 is moved to the chest wall side.

Since steps S107 and S108 are the same as in the processing of FIG. 9, the description thereof will be omitted.

Step S109A is the same processing as step S103A, and in a case in which the entire range is not scanned, the processing proceeds to step S106A, and in a case in which the entire range is scanned, the present routine ends.

As described above, in the present embodiment, in a case in which the operator manually performs the scanning using the ultrasound probe 50, and the ultrasound probe 50 is moved to the chest wall side, the ultrasound image is captured in the steer mode. As a result, the acquisition of the ultrasound image on the chest wall side is facilitated.

It should be noted that the configuration, the operation, and the like of the medical imaging system 100 described in the above-described embodiments are merely examples, and it goes without saying that the changes can be made depending on a situation within a range that does not depart from the gist of the present disclosure.

In regard to the embodiments described above, the following supplementary notes will be further disclosed.

Supplementary Note 1

A medical imaging apparatus comprising: a processor, in which the processor is configured to: acquire a position of an ultrasound probe that emits an ultrasound beam toward a breast of an examinee, which is in a compressed state via a compression plate; and in a case in which the position of the ultrasound probe in a direction orthogonal to a side surface of the compression plate on a chest wall side is equal to or smaller than a predetermined distance from the side surface and a predetermined switching condition is satisfied, perform control of switching to a steer mode or a trapezoidal mode in which an emission direction of the ultrasound beam is directed toward the chest wall side.

Supplementary Note 2

The medical imaging apparatus according to supplementary note 1, in which, in a case in which an inclination angle of the ultrasound beam emitted in the steer mode or the trapezoidal mode is denoted by θ, a depth of the breast to be observed is denoted by a, and a distance between the ultrasound probe and the compression plate is denoted by b, the predetermined distance is a distance represented by tan θ×(a+b).

Supplementary Note 3

The medical imaging apparatus according to supplementary note 1 or 2, in which the processor is configured to control a scanning mechanism that performs scanning using the ultrasound probe on the compression plate, and the switching condition is a case in which an instruction to stop capturing of an ultrasound image via the ultrasound probe is not received.

Supplementary Note 4

The medical imaging apparatus according to supplementary note 1 or 2, in which the processor is configured to: set a specific region to be irradiated with the ultrasound beam based on a radiation image captured by emitting radiation to the breast of the examinee; and control a scanning mechanism that performs scanning using the ultrasound probe on the compression plate, and the switching condition is a case in which capturing of an ultrasound image via the ultrasound probe is not performed on the specific region.

Supplementary Note 5

The medical imaging apparatus according to supplementary note 1 or 2, in which the switching condition is a case in which an instruction to stop capturing of an ultrasound image via the ultrasound probe is not received.

Supplementary Note 6

The medical imaging apparatus according to any one of supplementary notes 1 to 5, in which the compression plate includes a guide member that guides the ultrasound probe such that a longitudinal direction of the ultrasound probe is a direction orthogonal to a chest wall.

Supplementary Note 7

The medical imaging apparatus according to any one of supplementary notes 1 to 5, in which the processor is configured to control a scanning mechanism that performs scanning using the ultrasound probe on the compression plate such that the scanning using the ultrasound probe is performed on the compression plate in a state in which a longitudinal direction of the ultrasound probe is in the direction orthogonal to the side surface of the ultrasound probe on the chest wall side.

Supplementary Note 8

The medical imaging apparatus according to any one of supplementary notes 1 to 7, in which an acoustic matching material is provided between the ultrasound probe and the compression plate.

Supplementary Note 9

The medical imaging apparatus according to supplementary note 8, in which a thickness of the acoustic matching material is 1 mm or larger and 10 mm or smaller.

Supplementary Note 10

The medical imaging apparatus according to supplementary note 8 or 9, in which a thickness of the acoustic matching material is larger as a distance to the chest wall is smaller.

Supplementary Note 11

The medical imaging apparatus according to any one of supplementary notes 1 to 10, in which the processor is configured to display, in a distinguishable manner on a display unit, a first imaging region imaged in a state in which the emission direction of the ultrasound beam is a normal direction and a second imaging region imaged in the steer mode or the trapezoidal mode in which the emission direction of the ultrasound beam is inclined, and display, on the display unit, a captured ultrasound image.

Supplementary Note 12

A medical imaging method comprising: via a computer, acquiring a position of an ultrasound probe that emits an ultrasound beam toward a breast of an examinee, which is in a compressed state via a compression plate; and performing, in a case in which the position of the ultrasound probe in a direction orthogonal to a side surface of the compression plate on a chest wall side is equal to or smaller than a predetermined distance from the side surface and a predetermined switching condition is satisfied, control of switching to a steer mode or a trapezoidal mode in which an emission direction of the ultrasound beam is directed toward the chest wall side.

Supplementary Note 13

A medical imaging program causing a computer to execute a process comprising: acquiring a position of an ultrasound probe that emits an ultrasound beam toward a breast of an examinee, which is in a compressed state via a compression plate; and performing, in a case in which the position of the ultrasound probe in a direction orthogonal to a side surface of the compression plate on a chest wall side is equal to or smaller than a predetermined distance from the side surface and a predetermined switching condition is satisfied, control of switching to a steer mode or a trapezoidal mode in which an emission direction of the ultrasound beam is directed toward the chest wall side.

Supplementary Note 14

A medical imaging system comprising: a mammography apparatus that captures a radiation image by detecting radiation, which is emitted from a radiation source and is transmitted through a breast of an examinee, via a radiation detector; an ultrasound probe that emits an ultrasound beam to the breast of the examinee; and the medical imaging apparatus according to any one of supplementary notes 1 to 11.

What is claimed is:

1. A medical imaging apparatus comprising:
- a position detection sensor; and
- a processor,
- wherein the processor is configured to:
  - acquire from the position detection sensor, a position of an ultrasound probe that emits an ultrasound beam toward a breast of an examinee, which is in a compressed state via a compression plate;
  - detect a distance in a direction orthogonal to a side surface of the compression plate on a chest wall side to the ultrasound probe based on the position of the ultrasound probe; and
  - when the distance is equal to or smaller than a predetermined distance from the side surface, the processor controls switching to a steer mode or a trapezoidal mode in which an emission direction of the ultrasound beam is directed toward the chest wall side.

2. The medical imaging apparatus according to claim 1, wherein, when an inclination angle of the ultrasound beam emitted in the steer mode or the trapezoidal mode is denoted by θ, a depth of the breast to be observed is denoted by a, and a distance between the ultrasound probe and the compression plate is denoted by b, wherein the predetermined distance used to determine switching of the emission direction of the ultrasound beam is represented by tan θ×(a+b).

3. The medical imaging apparatus according to claim 1, wherein the processor is configured to control a scanning mechanism that performs scanning using the ultrasound probe on the compression plate, and when the distance is equal to or smaller than a predetermined distance from the side surface and when an instruction to stop capturing of an ultrasound image via the ultrasound probe is not received, the processor controls switching to a steer mode or a trapezoidal mode in which an emission direction of the ultrasound beam is directed toward the chest wall side.

4. The medical imaging apparatus according to claim 1, wherein the processor is configured to:

set a specific region to be irradiated with the ultrasound beam based on a radiation image captured by emitting radiation to the breast of the examinee; and control a scanning mechanism that performs scanning using the ultrasound probe on the compression plate, and when the distance is equal to or smaller than a predetermined distance from the side surface and when the ultrasound probe has not captured an ultrasound image of the specific region, the processor controls switching to a steer mode or a trapezoidal mode in which an emission direction of the ultrasound beam is directed toward the chest wall side.

5. The medical imaging apparatus according to claim 1, wherein the processor is configured to:

when the distance is equal to or smaller than a predetermined distance from the side surface and when an instruction to stop capturing of an ultrasound image via the ultrasound probe is not received, the processor controls switching to a steer mode or a trapezoidal mode in which an emission direction of the ultrasound beam is directed toward the chest wall side.

6. The medical imaging apparatus according to claim 1, wherein the compression plate includes a guide member that guides the ultrasound probe such that a longitudinal direction of the ultrasound probe is a direction orthogonal to a chest wall.

7. The medical imaging apparatus according to claim 1, wherein the processor is configured to control a scanning mechanism that performs scanning using the ultrasound probe on the compression plate such that the scanning using the ultrasound probe is performed on the compression plate in a state in which a longitudinal direction of the ultrasound probe is in the direction orthogonal to the side surface of the ultrasound probe on the chest wall side.

8. The medical imaging apparatus according to claim 1, wherein an acoustic matching material is provided between the ultrasound probe and the compression plate.

9. The medical imaging apparatus according to claim 8, wherein a thickness of the acoustic matching material is 1 mm or larger and 10 mm or smaller.

10. The medical imaging apparatus according to claim 8, wherein a thickness of the acoustic matching material is larger as a distance to the chest wall is smaller.

11. The medical imaging apparatus according to claim 1, wherein the processor is configured to display, in a distinguishable manner on a display unit, a first imaging region imaged in a state in which the emission direction of the ultrasound beam is a normal direction and a second imaging region imaged in the steer mode or the trapezoidal mode in which the emission direction of the ultrasound beam is inclined, and display, on the display unit, a captured ultrasound image, wherein the processor is configured to control emission of the ultrasound beam from the ultrasound probe and to generate and display the first imaging region and the second imaging region based on the controlled emission direction of the ultrasound beam.

12. A medical imaging system comprising:

a mammography apparatus that captures a radiation image by detecting radiation, which is emitted from a radiation source and is transmitted through a breast of an examinee, via a radiation detector;

an ultrasound probe that emits an ultrasound beam to the breast of the examinee; and the medical imaging apparatus according to claim 1.

13. A medical imaging method for a medical imaging apparatus including a computer and a position detection sensor, the method comprising:

via the computer, acquiring from the position detection sensor, a position of an ultrasound probe that emits an ultrasound beam toward a breast of an examinee, which is in a compressed state via a compression plate;

detecting a distance in a direction orthogonal to a side surface of the compression plate on a chest wall side to the ultrasound probe based on the position of the ultrasound probe; and performing, when the distance is equal to or smaller than a predetermined distance from the side surface, control switching to a steer mode or a trapezoidal mode in which an emission direction of the ultrasound beam is directed toward the chest wall side.

14. A non-transitory computer-readable storage medium storing a medical imaging program causing a computer to execute a process comprising:

acquiring from a position detection sensor, a position of an ultrasound probe that emits an ultrasound beam toward a breast of an examinee, which is in a compressed state via a compression plate;

detect a distance in a direction orthogonal to a side surface of the compression plate on a chest wall side to the ultrasound probe based on the position of the ultrasound probe; and performing, when the distance is equal to or smaller than a predetermined distance from the side surface, control switching to a steer mode or a trapezoidal mode in which an emission direction of the ultrasound beam is directed toward the chest wall side.

* * * * *